(12) United States Patent
Lyman et al.

(10) Patent No.: US 11,445,982 B2
(45) Date of Patent: Sep. 20, 2022

(54) METHOD AND APPARATUS FOR DETERMINING BLOOD PRESSURE ON MEASURED HEART SOUNDS

(71) Applicant: Wayne State University, Detroit, MI (US)

(72) Inventors: William D. Lyman, Los Angeles, CA (US); Gaurav Kapur, Troy, MI (US); Yong Xu, Troy, MI (US); Sean F. Wu, Troy, MI (US); Lingguang Chen, Troy, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 16/484,608

(22) PCT Filed: Feb. 7, 2018

(86) PCT No.: PCT/US2018/017178
§ 371 (c)(1),
(2) Date: Aug. 8, 2019

(87) PCT Pub. No.: WO2018/148251
PCT Pub. Date: Aug. 16, 2018

(65) Prior Publication Data
US 2020/0022659 A1 Jan. 23, 2020

Related U.S. Application Data

(60) Provisional application No. 62/456,354, filed on Feb. 8, 2017.

(51) Int. Cl.
*A61B 5/00* (2006.01)
*A61B 5/0205* (2006.01)
(Continued)

(52) U.S. Cl.
CPC .......... *A61B 5/7278* (2013.01); *A61B 5/0205* (2013.01); *A61B 5/7203* (2013.01);
(Continued)

(58) Field of Classification Search
CPC ... A61B 5/7278; A61B 5/0205; A61B 5/7203; A61B 7/04; A61B 5/021; A61B 5/024
See application file for complete search history.

(56) References Cited

U.S. PATENT DOCUMENTS

2003/0083582 A1* 5/2003 Hirsh ................. A61B 5/02028
600/509
2003/0095263 A1* 5/2003 Varshneya ............. A61B 5/002
356/477
(Continued)

OTHER PUBLICATIONS

T. Tsalaile, S.M. Naqvi, K. Nazarpour, S. Sanei, J.A. Chambers, "Blind Source Extraction of Heart Sound Signals from Lung Sound Recordings Exploiting Periodicity of the Heart Sound," Acoustics, Speech and Signal Processing, 2008. ICASSP 2008. IEEE International Conference on, 2008, pp. 461-464.
(Continued)

*Primary Examiner* — Amanda K Hulbert
*Assistant Examiner* — Natasha Patel
(74) *Attorney, Agent, or Firm* — Fishman Stewart PLLC

(57) ABSTRACT

A system and method of determining blood pressure includes measuring heart sounds, separating the measured heart sounds into a first heart sound ($S_1$) and a second heart sound ($S_2$), mathematically characterizing $S_1$ and $S_2$, and determining a blood pressure based on the characterization.

20 Claims, 19 Drawing Sheets

(51) Int. Cl.
    *A61B 7/04* (2006.01)
    *A61B 5/021* (2006.01)
    *A61B 5/024* (2006.01)
(52) U.S. Cl.
    CPC ............ *A61B 7/04* (2013.01); *A61B 5/021* (2013.01); *A61B 5/024* (2013.01)

(56) References Cited

U.S. PATENT DOCUMENTS

| | | | |
|---|---|---|---|
| 2004/0167417 A1* | 8/2004 | Schulhauser | A61B 7/003 600/513 |
| 2007/0276270 A1* | 11/2007 | Tran | A61B 5/0022 600/508 |
| 2008/0154144 A1* | 6/2008 | Unver | A61B 5/02028 600/528 |
| 2009/0062665 A1 | 3/2009 | Peretto et al. | |
| 2011/0066041 A1* | 3/2011 | Pandia | A61B 5/029 600/484 |

OTHER PUBLICATIONS

H. Liang, L. Sakari, H. Iiro, "A Heart Sound Segmentation Algorithm Using Wavelet Decomposition and Reconstruction," Engineering in Medicine and Biology Society, 1997. Proceedings of the 19th Annual International Conference of the IEEE, 1997, pp. 1630-1633 vol. 1634.

X. Jingping, L.G. Durand, P. Pibarot, "Nonlinear Tansient Chirp Signal Modeling of the Aortic and Pulmonary Components of the Second Heart Sound," IEEE Transactions on Biomedical Engineering, vol. 47 (Jul. 2000), pp. 1328-1335.

S. Choi, Z. Jiang, "Development of Wireless Heart Sound Acquisition System for Screening Heart Valvular Disorder," Proceedings of the Int'l Conf. on Instrument.,Control and Info.Tech. (SICE 2005), Okayama, Japan, 2005, pp. 3771-3776.

A. Belouchrani, K. AbedMeraim, J. F. Cardoso, and E. Moulines, "A Blind Source Separation Technique Using Second-Order Statistics," IEEE Trans. Signal Process., vol. 45, No. 2, pp. 434-444 (Feb. 1997).

C.C. Vayá, J.J. Rieta, C. Sánchez, and D. Moratal, "Performance Study of Convolutive BSS Algorithms Applied to the Electrocardiogram of Atrial Fibrillation," Int'l. Conf. on Ind. Component Analysis and Signal Separation, Springer, pp. 495-502 (2006).

H. Saruwatari, S. Kurita, K. Takeda, F. Itakura, T. Nishikawa and K. Shikano, "Blind Source Separation Combining Independent Component Analysis and Beamforming," EURASIP Journal on Applied Signal Processing, pp. 1135-1146 (2003).

YY. Yang and S. Nagarajaiah, "Time-Frequency Blind Source Separation Using Independent Component Analysis for Output-Only Modal Identification of Highly Damped Structures," Journal of Structural Engineering, vol. 139, pp. 1780-1793 (2012).

A. Cichocki, R. Zdunek and S.-i. Amari, "New Algorithms for Non-Negative Matrix Factorization in Applications to Blind Source Separation," 2006 IEEE International Conference on Acoustics Speech and Signal Processing Proceedings, IEEE, pp. V-V (2006).

L. Parra and P. Sajda, "Blind Source Separation Via Generalized Eigenvalue Decomposition," Journal of Machine Learning Research, vol. 4, pp. 1261-1269 (2003).

S. F. Wu and N. Zhu, "Blind Extraction and Localization of Sound Sources Using Point Sources Based Approaches," Journal of the Acoustical Society of America, vol. 132, Aug. 2012, pp. 904-917.

C. Xie-feng, J. Bin, Y. He, G. YuFeng, Z. ShaoBai.: "A New Method of Heart Sound Signal Analysis Based on Independent Function Element", AIP Advances, American Institute of Physics, vol. 4, No. 9, Sep. 22, 2014, XP012190107, DOI: 10.1063/1.4896407.

Z. Tong, I. Qadar, F. Abu-Amara "Heart Sound Separation Using Fast Independent Component Analysis", 2015 International Conference on Developments of E-Systems Engineering (DESE), IEEE, Dec. 13, 2015 (Dec. 13, 2015), pp. 3-6, XP032958761, DOI: 10.1109/DESE.2015.38, ISBN: 978-1-5090-1860-4.

V. Nigam, R. Priemer "A dynamic method to estimate the time split between the A2 and P2 components of the S2 heart sound", Physiological Measurement, Institute of Physics Publishing, vol. 27, No. 7, Jul. 1, 2006 (Jul. 1, 2006), pp. 553-567, XP020105784, ISSN: 0967-3334, DOI: 10.1088/0967-3334/27/7/001 Sections 2.1, 2.2, 3.1; figure 3.

International Search Report for PCT/US2018/017178 dated May 14, 2018.

* cited by examiner

METHOD AND APPARATUS FOR DETERMINING BLOOD PRESSURE ON MEASURED HEART SOUNDS

CROSS-REFERENCE TO RELATED APPLICATIONS

This application claims priority to International Patent Application PCT/US2018/0171078 filed Feb. 7, 2018, which claims priority to U.S. Provisional Patent Application Ser. No. 62/456,354 filed Feb. 8, 2017, the contents of which are hereby incorporated by reference in their entirety.

BACKGROUND

The current standard technique gold standard for random/intermittent blood pressure (BP) determination is by using cuff method (with stethoscope or by oscillometric method), which may not be optimally suited for infants or children. Even for adults such an approach yields reduced accuracy with respect to intra-arterial blood pressure measurements. Some limitations and inaccuracies in BP measurement by the cuff (stethoscope or oscillometric) method relate to 1) availability of appropriate cuff size [especially true and a concern in pediatrics]; 2) confusion regarding the Kortkoff sounds (sounds auscultated with a stethoscope placed over the brachial artery when checking BP by mercury/aneroid sphygmomanometers); 3) effect of body and arm position when recording BP; 4) appropriate cuff placement; 5) maintenance of the system while ensuring airtight inflation and deflation of the cuff; 6) maintaining a deflation rate of 2-3 mm Hg per second; and, 7) for auscultation, differences in testers' hearing sensitivities. Moreover, it does not allow for continuous monitoring of blood pressures over days, or more. Continuous blood pressure measurements are necessary in the treatment of very sick patients inside intensive care unit (ICU) and under surgical operations, as fluctuations in hemodynamic status associated with low blood pressure (indicating poor perfusion) have been linked to poor outcomes. The current standard for continuous BP measurements is via invasive intra-arterial cannulation, and the available non-invasive alternatives can be very expensive with questionable sensitivity.

According to one standard, invasive arterial cannulation with continuous BP monitoring is an invasive procedure that involves cannulation and placement of intra-arterial transducers. Sources of measurement error associated with this technique include: 1) an inaccurate transducer level (raising or lowering the transducer by 10 cm can introduce errors of 7.5 mmHG with BP measurement); and 2) regular zeroing/flushing for accurate readings. Besides the technical expertise used for these procedures, complications could happen, which include but are not limited to: 1) bleeding; 2) thrombosis; 3) hematoma; 4) vascular infection; 5) vascular compromise with digital necrosis; 6) nerve damage and accidental injections of air, thrombus, or hyperosmolar solutions; 7) AV fistulae; and 8) carpal tunnel syndrome.

According to another standard, non-invasive continuous BP monitoring may be based on the known Peñáz Principal, wherein a small finger cuff containing a photoplethysmograph—a light source on one side of the cuff and infrared receiver on the opposite side—with the ability to estimate the blood volume of the finger via the infrared light absorbance. A signal obtained is used in a feedback loop allowing for adjustment of the cuff to keep blood volume constant. "Finapres" (an acronym for FINger Arterial PRESsure; based on this principal) assumes the cuff pressure is equal to arterial pressure and then using a formula to reconstruct brachial artery pressures.

This technique has been validated against intra-arterial BP measurement. However, known sources of error in this approach include, but are not limited to: 1) availability of appropriate cuff size (especially true and a concern in pediatrics); 2) confusion regarding Kortkoff sounds (sounds auscultated with a stethoscope placed over the brachial artery when checking BP by mercury/aneroid sphygmomanometers); 3) effect of body and arm position when recording BP; 4) appropriate cuff placement; 5) maintenance of the system while ensuring airtight inflation and deflation of the cuff; 6) maintaining a deflation rate of, for instance, 2-3 mm Hg per second; and, 7) for auscultation, differences in testers' hearing sensitivities.

Another approach is calibrating the Peñáz-technique values with a non-invasive cuff placed on the upper arm CNAPTM (upper arm calibration).

However, states causing low peripheral perfusion (as is commonly encountered in very sick patients) reduce the ability of the feedback system to function appropriately. In fact, vascular disease, cold temperature, Raynaud's disease as well as other factors may contribute to finger plethysmogram failure. Systemic vasoactive drugs (also used routinely in patients needing continuous monitoring) also have a role in inducing error in these devices.

Devices for measurement of blood pressure by occluding a digital artery in the finger are generally not preferred because limb position and peripheral vasoconstriction may affect the accuracy of this technique.

Another known approach includes the use of tonometry, in which a pressure transducer is placed on the skin and measures arterial blood pressure via contact pressure. Tonometry includes a calibration step via an initial blood pressure measurement by another technique that may be considered inaccurate. Despite being available for a longer time than the Peñáz technique, tonometry is not widely used due to concerns for its ability to detect rapid and large transient changes in blood pressure.

Another known technique involves measuring pulse transit time. Pulse transducers are positioned at two different sites and record the time of travel for an arterial wave between two points. However, it may be difficult to correlate pulse transit time to blood pressure.

BP may be indirectly measured using a cuff-based method. However, such methods are not typically preferred and may not be appropriate for critically ill, hemodynamically unstable, or patients on vasoactive drugs, when relatively minor inaccuracies in pressure can have a significant clinical consequences and impact therapeutic decision making.

Thus, there is a need for improved methods of measuring BP. Some more commonly available and used non-invasive methods, while safe and relevant, may not be an accurate or precise standard of measurement for such an important indicator of individual health. The more preferred invasive method for critically ill children may be associated with significant complications and limitations. And, although the current methods of BP measurements and monitoring have been used to make diagnosis and treatment decisions for many years, the need for having an accurate measurement of BP to improve patient care is still relevant and important.

Thus, there is a need for improvement of blood pressure monitoring.

BRIEF DESCRIPTION OF THE DRAWINGS

Other objects, features, and advantages of the present disclosure will be readily appreciated as the same becomes better understood after reading the subsequent description taken in connection with the accompanying drawing wherein.

DETAILED DESCRIPTION

Figure 1:
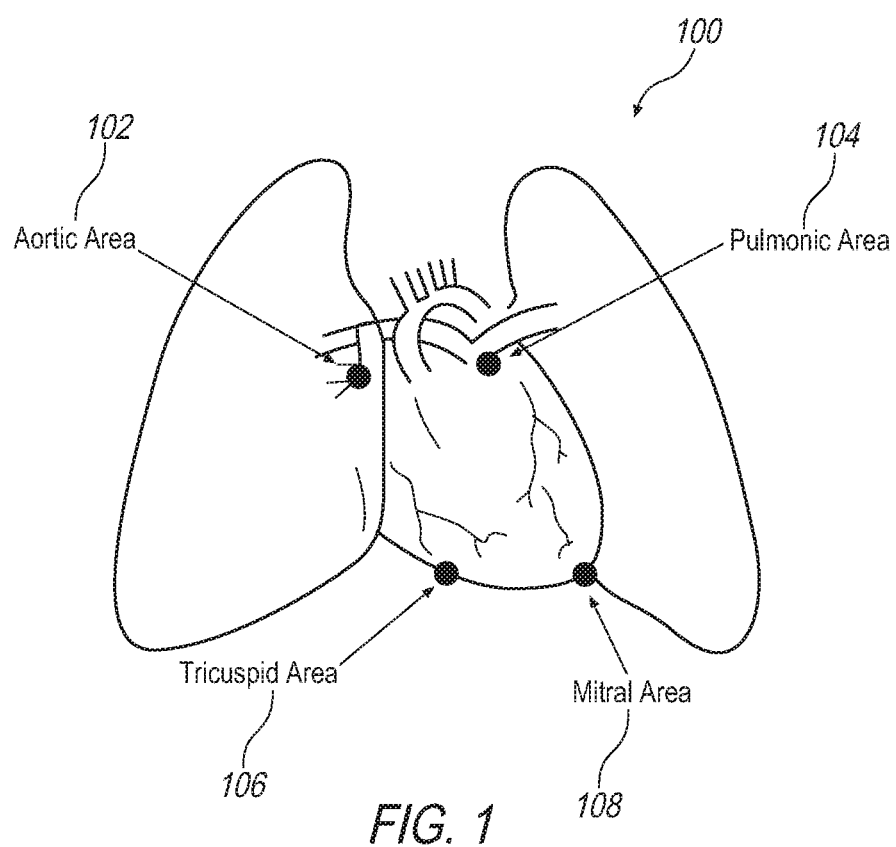
FIG. 1 is an illustration of a heart, showing aortic, pulmonic, tricuspid, and mitral areas.

A methodology is disclosed that enables calculation of the systolic and diastolic blood pressures continuously in a non-invasive manner, based on the heart sounds measured from the chest of a human being. To this end, first and second heart sounds, known as $S_1$ and $S_2$, are separated from directly measured heart sound signals. Next, individual characteristics of $S_1$ and $S_2$ are identified and correlated to systolic and diastolic blood pressures. As known, material properties of a human being are inhomogeneous, changing from one organ to another, and the speed at which the heart sound signals propagate inside a human body cannot always be determined precisely. Moreover, the exact locations from which the heart sounds are originated are estimated. As such, the disclosed method is semi-empirical. Yet, validation results have demonstrated that this semi-empirical computer model can produce robust and accurate calculations of the systolic and diastolic blood pressures.

The disclosed technique is non-invasive and is useful for not only children, but also for adults for; 1) continuous noninvasive BP monitoring and anesthesia monitoring, for which the current continuous BP monitoring is done through invasive arterial line and 2) intermittent/random BP measurement in offices, clinics, emergency room or home. The disclosed noninvasive continuous BP measurement allows for easy, sensitive and reliable continuous measure of BP. The disclosed method provides an alternative to the currently known methods, such as a cuff method of blood pressure measurement in an intensive care unit. The disclosed BP measuring technology may also be implemented as a reliable tool for BP measurement in any setting such as outpatient clinic, emergency rooms or patient home with further implications for mobile (smart phone) based health care.

According to the disclosure, analyzing heart sounds and correlating them to BP yield a more accurate way of measuring and monitoring BP. Heart sounds are much easier to measure by using an accelerometer designed with a decoupled piezoresistive layer than conventional methods. Moreover, the disclosed technique is non-invasive and suitable for children and adults.

The disclosed technique calculates BP based on heart sounds. Important advantages of the disclosure are that: 1) heart sounds are much easier and more reliable to measure, regardless of the patient's age, size, sex, etc.; 2) the measurement device is easy to apply and BP calculations have statistically-significant accuracy, precision, specificity and sensitivity; and 3) will reduce, if not eliminate, existing variability in BP measurements by the current methods.

The disclosed technique can be readily implemented by taping a few transducers on the chest area of a patient, and the heart sounds can be measured and transmitted through, for instance, wireless Internet to a central monitoring system. Acquired data is processed using disclosed technologies to reduce or eliminate random background noise and interfering signals, and to extract intracardiac sounds (i.e., sounds that are associated with heart value openings and closings). The intracardiac sounds are then fed into a mathematical model to calculate BP values. One important feature of the disclosed material is that it enables one to conduct remote, wireless and continuous monitoring of BP values of any patient.

Disclosed also is an ambulatory BP tele monitoring system, which enables calculation and monitoring of systolic and diastolic BP continuously based on the heart sounds measured directly on the chest of any human being. To this end, three tasks related to the disclosure include: 1) cleanse data; 2) extract target features of denoised signals; and 3) calculate BP values, the accuracy and precision of which have been confirmed using Critical Care patient data.

Cleansing Heart Sounds

Referring to FIG. 1, an illustration of a heart 100 shows aortic 102, pulmonic 104, tricuspid 106, and mitral 108 areas. Normal heart sounds include a first heart sound ($S_1$) and the second heart sound ($S_2$). Each of the heart sounds includes two components that are attributable to different heart valves. For example, $S_1$ includes two components that are linked to mitral and tricuspid valve closures, designated as M1 and T1 respectively. Similarly, $S_2$ includes two components that are generated by aortic and pulmonary valve closures, designated as A2 and P2 respectively. Both $S_1$ and $S_2$ are readily detectable, but the components of $S_1$ and $S_2$ can be difficult to discern, but best measured near aortic, pulmonic, tricuspid and mitral areas, respectively as shown in FIG. 1.

Generally, A2 and P2 sounds are susceptible to lung sound inferences, which are due to at least in part to airflow during inhalation and exhalation. Lung sound can be heard throughout the thoracic cavity area. The frequency range of normal lung sound ranges approximately from 50 to 500 Hz, and that of heart sound is approximately from 25 Hz to 250 Hz. As such, the heart and lung sounds overlap each other not only in time, but also in frequency. On the other hand, the heart sounds collected from tricuspid and mitral are not as severely affected by lung sounds.

Figure 2:
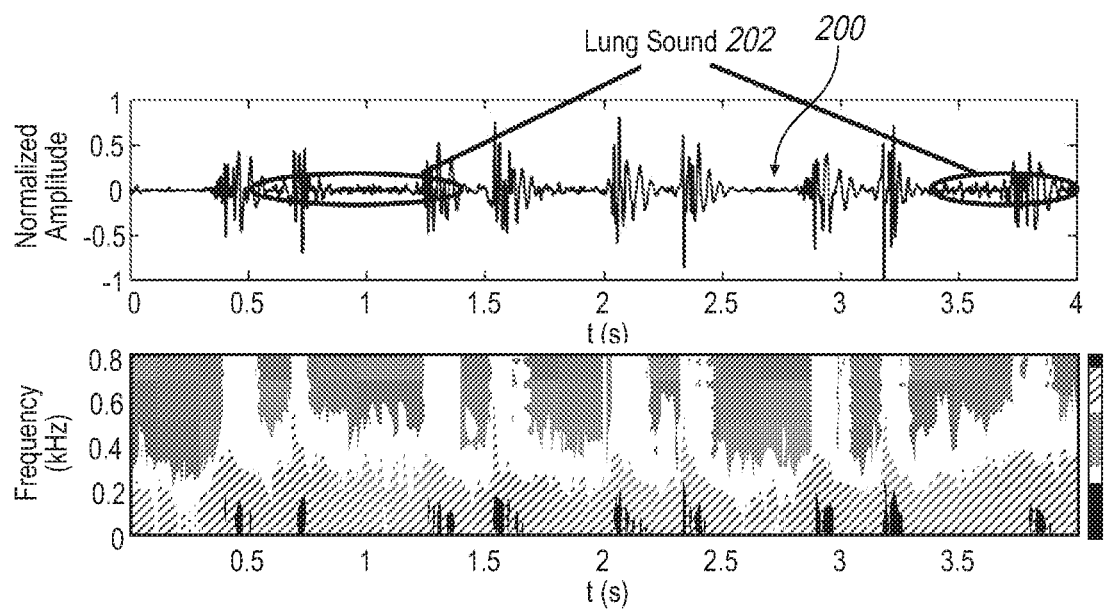
FIG. 2 illustrates normalized heart sound signals collected from the mitral area.
Figure 3:
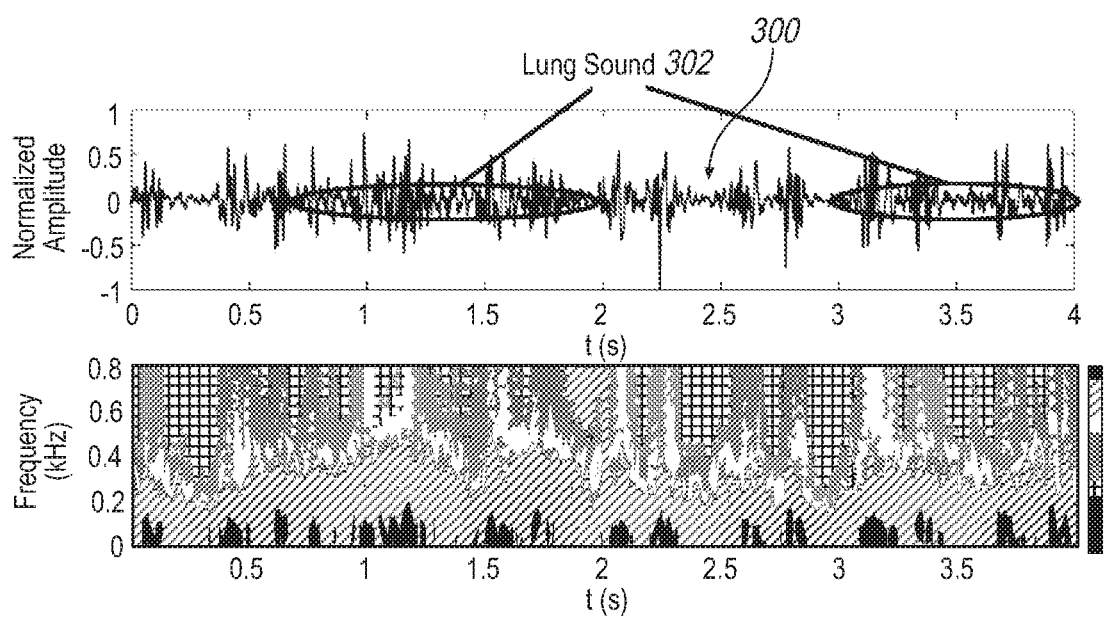
FIG. 3 illustrates normalized heart sound signals collected from the aortic area.

FIG. 2 and FIG. 3 illustrate some normalized heart sound signals collected from the mitral area and aortic area, respectively. Although the signal-to-noise ratio (SNR) of heart sounds in the mitral area are high, lung sound interferences can be seen from the time domain signal and spectrogram. FIGS. 2 and 3 show that heart sounds collected 200, 300 can be severely contaminated by lung sounds 202, 302. Thus, it is necessary to cleanse the heart sounds before analyzing them.

Note that the heart sounds are non-stationary, whose frequency contents vary from one cardiac cycle to another. Hence time and frequency domains are considered simultaneously by performing a time-frequency analysis. A basic time-frequency analysis may be performed via short-time Fourier transform (STFT). However, STFT may be ineffective because its resolution in frequency is tied to that in time. As a result, increasing the resolution in time to capture changes in the time domain comes at the expense of decreasing the resolution in the frequency, and vice versa. And, despite this tradeoff, it may still not possible to utilize STFT to denoise signals since heart sounds and lung sounds that have significant overlapping in the frequency domain.

Thus, a Discrete Wavelet Transform (DWT) may be utilized. Unlike STFT, DWT is generally immune from having entwined resolution in the frequency and time domains. For example, a dyadic grid of DWT can be applied to decompose signals into mutually orthogonal dilations and translations without any overlapping and redundancies in describing signals. This makes DWT an efficient and effective algorithm to pick out "coherent structures" of the heart sounds that are embedded in mixed data.

DWT-based denoising includes three steps: decomposition, scale-depend thresholding and reconstruction. In general, any known DWT may be chosen for denoising. However, according to the disclosure D4 Daubechies Wavelet is selected, as an example, to decompose the signals into eight scales. DWT is first used on segments of signal with relatively high signal-to-noise ratio (SNR) to acquire an understanding of the "coherent structure" of the heart sounds. The decomposed results indicate that the most significant "coherent structure" falls on scales 4, 5, and 6. Hence a Sure Shrink thresholding technique is used for these scales, which combines a universal threshold and Stein's unbiased estimate of risk, to eliminate uncoherent structures and extract heart sounds over the entire time record of signals. Subsequently, inverse DWT is used to reconstruct heart sounds.

Figure 4:
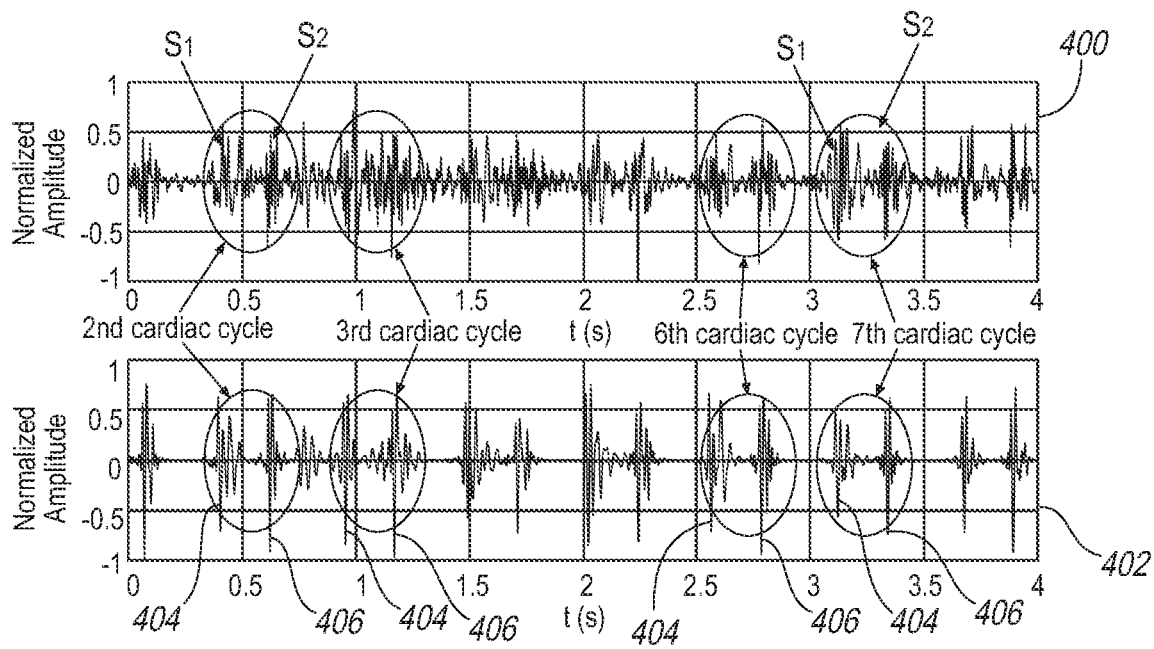
FIG. 4 illustrates heart beat signals before denoising and after denoising.

FIG. 4 illustrates heart beat signals before denoising 400 and after denoising 402 by using the D4 Daubechies Wavelet. The effects of cleansing lung sound and random noise are evident. In particular, $S_1$ 404 and $S_2$ 406 sounds are evident after denoising, in various representative cardiac cycles as shown. And, according to the disclosure, further signal processing will be conducted to extract the features involved in $S_1$ and $S_2$ sounds.

Extracting Features of Heart Sounds $S_1$ and $S_2$ sounds are separated various features associated with the individual components are extracted, according to the following.

The Heart Rate

To separate $S_1$ and $S_2$ sounds the heart rate is first determined by applying an autocorrelation function to the denoised heart sounds.

Figure 5:
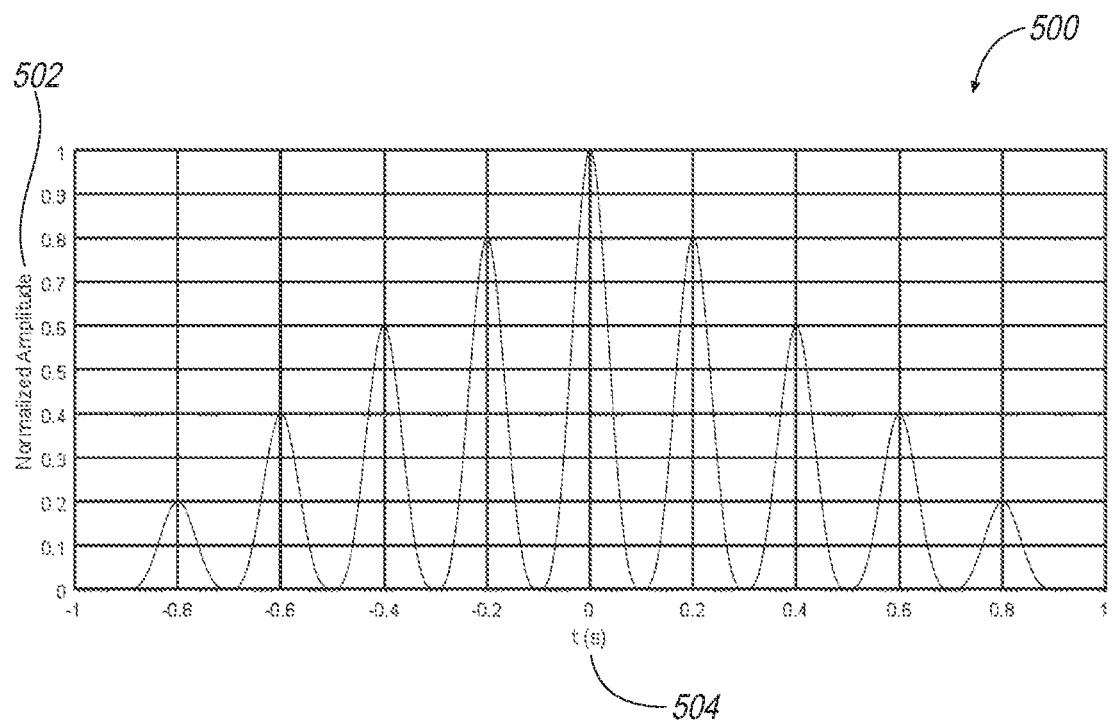
FIG. 5 depicts an example of applying autocorrelation to an amplitude modulated wave packet.

FIG. 5 depicts an example 500 of applying autocorrelation to an amplitude modulated wave packet. The vertical axis 502 shows the amplitude of autocorrelation coefficients, and the horizontal axis 504 is the time delay. The exemplary results indicate that the autocorrelation coefficients are maximal at the center (zero delay), which means that two signals are well correlated to each other when there is no delay in time. The amplitude of autocorrelation function decreases, however, as time delay (lead or lag) increases. Accordingly, these signals become less and less correlated to each other.

Figure 6:
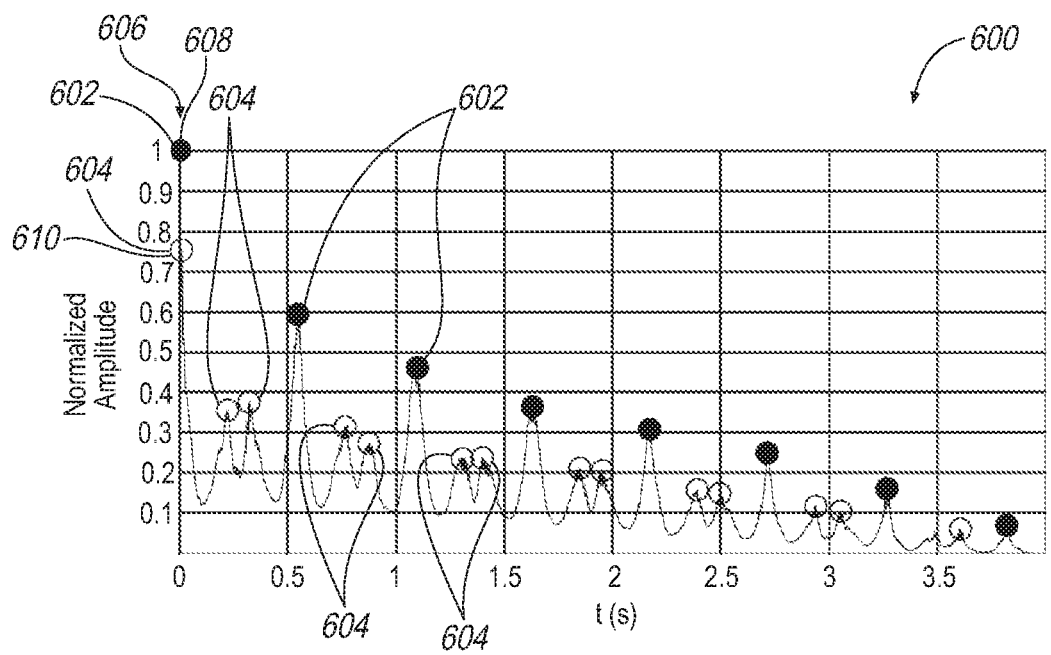
FIG. 6 illustrates correlation coefficients of denoised heart sounds.

According to the disclosure, autocorrelation to denoised heart sounds includes examining the autocorrelation coefficients. FIG. 6 illustrates autocorrelation coefficients 600 of denoised heart sounds. As indicated, there are multiple peaks as marked by solid dots 602 and circles 604. As seen, the autocorrelation coefficients for the solid dot and circle at no time delay are maximum 606: The former 608 is unity, and the latter 610 is 0.76. This means that without time delay S1 or the denoised heart sounds match well with themselves. Meanwhile, there is a high similarity between S1 and S2 sounds without time delay, but they are not the same. Hence, the autocorrelation coefficient is large but less than unity. As the time delay increases, S1 sound correlates itself not as well so its correlation decreases, and the value of the autocorrelation coefficient decays.

On the other hand, S1 and S2 sounds are only slightly correlated to each other. As such, the corresponding autocorrelation coefficients remain small for all time delays. Thus, the exemplary results indicate that solid dots 602 mark the occurrences of $S_1$ sound and may be used to estimate the heart rate. The intervals between two solid dots 602 are not the same, meaning that the heart rate is not a constant, which is common even for a healthy human being. To facilitate feature extraction, an average interval of solid dots is taken and used as an averaged heart rate.

To automate the computation processes, a computer readable storage medium having stored thereon a program may automatically pick out solid dots 602 while ignoring the circles 604. This may be accomplished by using a two-stage screening procedure. First, the smaller peak of any two consecutive peaks within a specific time interval may be discarded, having the larger peaks retained. According to one example, this may be achieved by moving a window function with its width fixed at a pre-determined time interval along the time axis.

For example, the heart rate of a normal human being may be considered as 90 per minute. Thus, in this example the corresponding window size can be set to 90/m, or 0.66 second per hear beat, which can eliminate smaller peaks. Next, the amplitudes of peaks are in a descending order, which may be done by numerically comparing the amplitudes of consecutive peaks. Once unwanted peaks are eliminated, the heart rate (HR) can be calculated by taking an average of all intervals of the remaining peaks.

Segmentation of Heart Sounds

Heart sound segmentation plays an important role in automatic heart sounds feature extraction, because through segmentation an occurrence and duration of $S_1$ and $S_2$ can be specified from contiguous cardiac cycles. The highly impulsive nature of heart rates makes it possible to segment heart sounds. However, this can create a challenge in a computing solution, because there are multiple pulses in heart sounds that depict both $S_1$ and $S_2$ sounds.

A conventional segmentation approach can be achieved by enveloping packets of impulses that describe $S_1$ and $S_2$ sounds. Several envelope algorithms have been developed for segmenting heart sounds, which include the normalized average Shannon energy method, Hilbert transform based envelop, cardiac characteristic waveform algorithm, etc. For approximately normal heart sound signals with a high SNR, $S_1$ and $S_2$ components can be extracted via envelopes by applying a simple threshold. However, problems can arise when SNR is low or heart sound signals are irregular.

Figure 7:
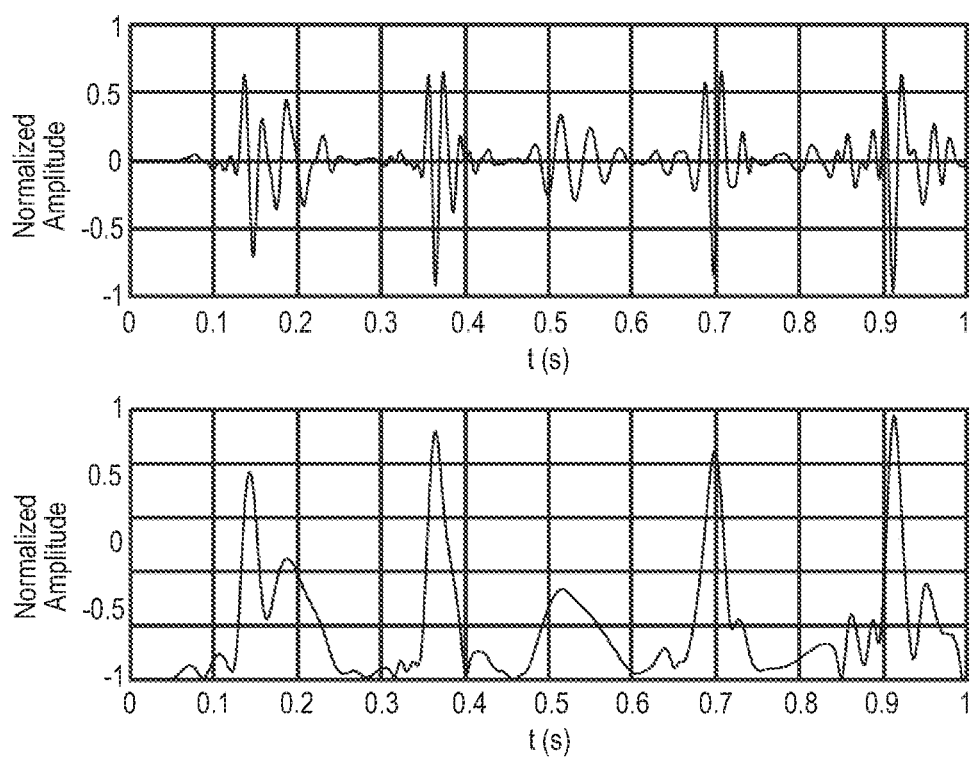
FIG. 7 illustrates the 2nd and 3rd cardiac cycles as seen in FIG. 4.
Figure 8:
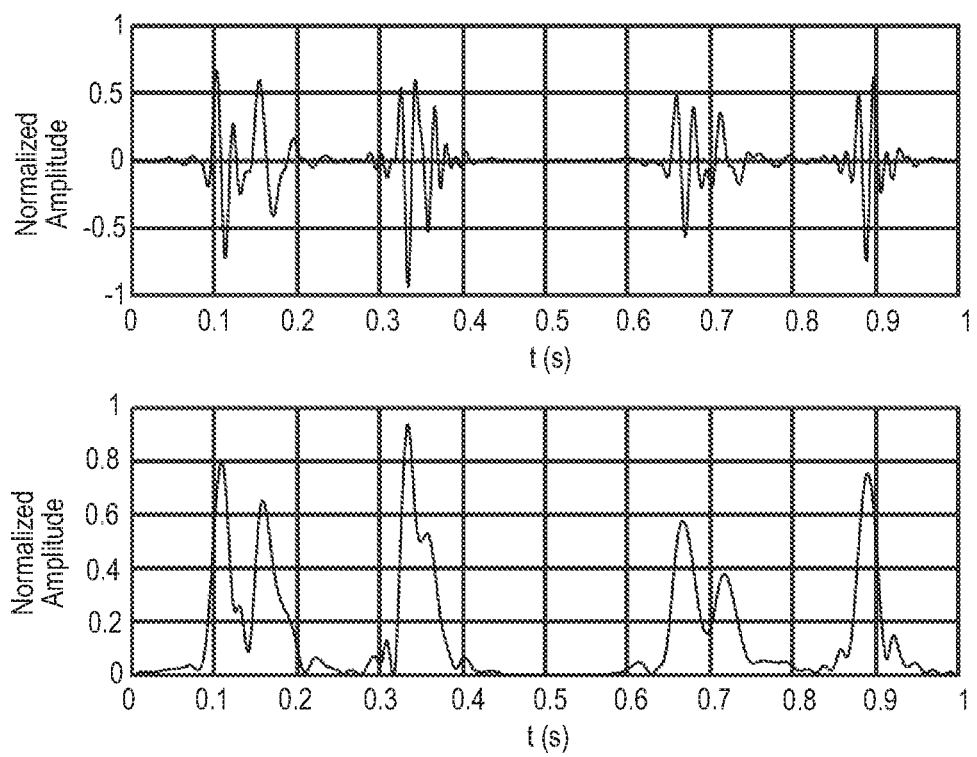
FIG. 8 illustrates the 6th and 7th cardiac cycles from FIG. 4.

For instance, using aortic area heart sounds as an example, FIG. 7 illustrates the 2nd and 3rd cardiac cycles as seen in FIG. 4 with envelopes applied to irregular peaks around 0.5 second, having heart sounds with abnormal components. FIG. 8 illustrates the 6th and 7th cardiac cycles from FIG. 4 after application of envelopes, having heart sound signals with split $S_1$. In these examples, there are split components in $S_1$ sound, which makes it difficult to automate the process of identifying $S_1$ and $S_2$ sounds correctly.

According to the disclosure a novel segmentation method is disclosed. This disclosed algorithm is applied to selected peaks separated by specific time intervals of original heart sounds. First, the peaks that indicate $S_1$ and $S_2$ sounds, together with their duration, are identified. Next, durations of systole and diastole are calculated. The procedures to determinate these parameters can be summarized in the following two steps 1. Resampling Signals Based on Peak Detection A downscaling process enables elimination of the enveloping function in conventional methods. The enveloping function is equivalent to interpolation to find extra values among selected discrete peaks. However, even after enveloping, peak detection is still performed. As such, discrete local maxima are used to represent core features of heart sounds.

During resampling, a window function of a fixed length is moved in the time axis. The window function enables picking out the highest local maximum, and then discarding the rest of the data. The length of the window is governed by the highest frequency of interest. From the known Nyquist sampling theorem, the sampling rate should be higher than at least twice the highest frequency of interest. Under this setting, resampling minimizes the interval among peaks. Meanwhile, a majority of normal heart sounds are typically found to be in the range of 25 to 90 Hz. As such, the resampling rate can be set at 220 Hz, which is about 2.5 times the higher frequency of 90 Hz. The corresponding length of the resampling window is therefore 0.0045 second (1/220 Hz). It should be noted that the local maxima do not necessarily exist inside every window. Thus, by applying this window function, undesirable noise embedded in the heart sound can be removed, and only the peaks separated by a specific time interval are kept.

2. Identifying $S_1$ and $S_2$ Sounds

To identify individual components, a maximum peak is determined in each cardiac cycle, regardless whether this maximum peak denotes the first or second heart sound, which can be achieved by using the peak detection method described. The heart rate determined earlier defines the window length and the resampling process described yields a set of new peaks. Next, the duration of the selected heart sound components is determined. Based on the maximum peak at the center, boundaries for each peak are determined through an approximation process. In this example, it is assumed that the duration of $S_1$ and $S_2$ ranges from 0.1 to 0.3 second.

Figure 9:
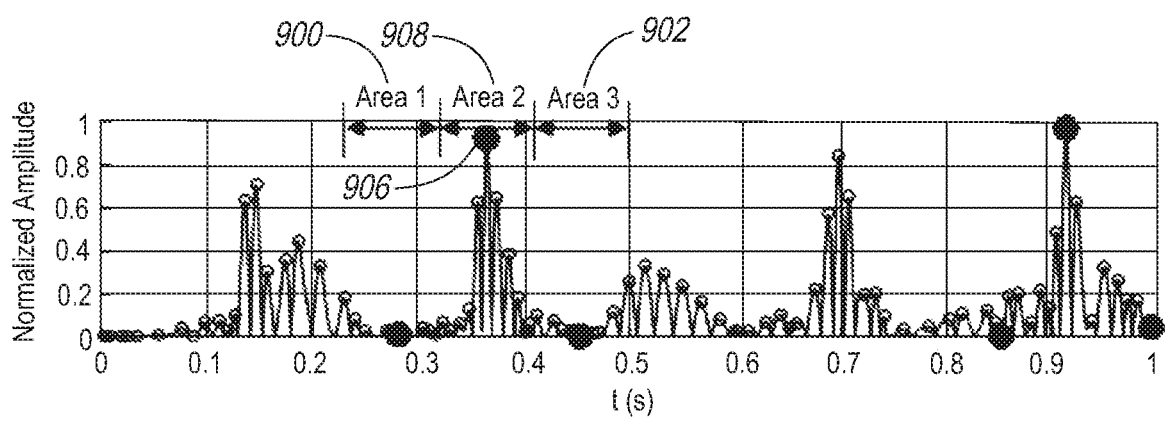
FIG. 9 illustrates exemplary portions of the cardiac cycle having various portions of the cardiac cycle identified for identifying components of the heart sounds.

FIG. 9 illustrates exemplary portions of the cardiac cycle having various portions of the cardiac cycle identified for identifying components of the heart sounds. Beginning with search areas marked as Area 1 and Area 3 in FIG. 9, search for the minimum values in Area 1 900 and Area 3 902 as indicated by two solid black dots 904. The third solid black dot 906 is placed at the maximum value in Area 2 908, whose length is set to be 0.1 second, in this example. The duration between the two solid black dots 904 implies one component of heart sounds, and this component appears again after one heartbeat as shown in FIG. 9. The duration of all Area 2 908 is 0.1 second, which is surrounded by Area 1 900 and Area 3 902 on both sides. This process is repeated until this component of heart sounds is identified over the relevant time record.

Figure 10:
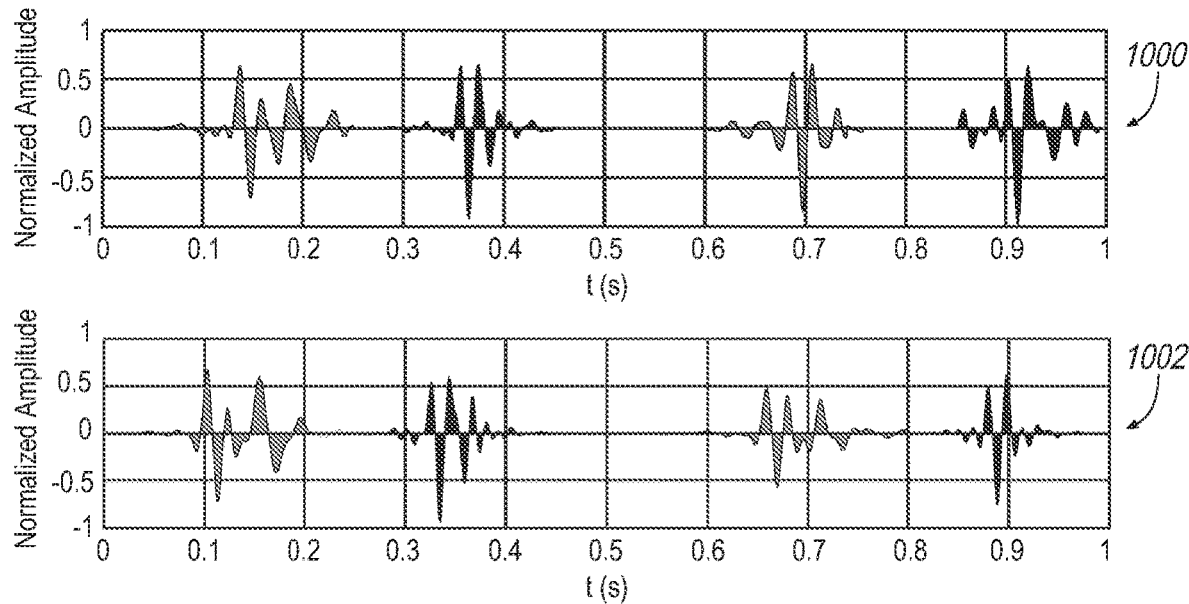
FIG. 10 shows segmentation results of FIG. 7 and FIG. 8.

Until now, only one component of heart sounds has been specified within one cardiac cycle. To find another component, the same procedure as described above is followed to eliminate peaks within other detected peaks. FIG. 10 shows the segmentation results of FIG. 7 1000 and FIG. 8 1002. Once both components are identified, $S_1$ and $S_2$ sounds are discerned. To this end, another assumption is made: the systole duration is shorter than the diastole duration. In other words, the interval of $S_1$ to $S_2$ must be smaller than that of $S_2$ to $S_1$. Using this assumption, $S_1$ and $S_2$ are readily defined.

Growth and Decay Rate

Figure 11:
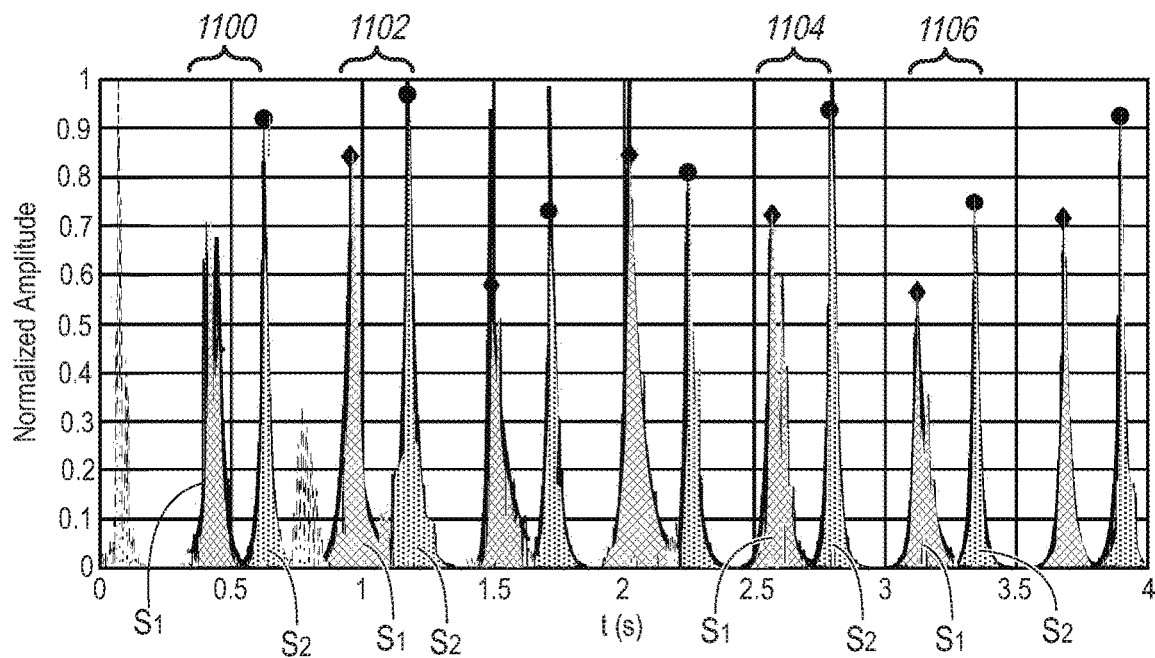
FIG. 11 shows exemplary exponential growth and decay curves.

Thus far, several time domain features including heart rate, durations of $S_1$ and $S_2$, and interval between $S_1$ and $S_2$ have been identified. In addition to these features, rates of growth and decay of each component are determined. For example, FIG. 9 depicts that the amplitudes of peaks in Area 2 grow from near zero to a maximum value and then decay to near zero again. This phenomenon repeats itself in all packets. Because heart sounds are associated with the open and closure of specific heart valves and since the blood is a viscous fluid, it is plausible to use an exponential function to describe these grows and decays. It is contemplated, however, that other growth and decay mathematical models may be used. Mathematically, the exponential function is expressed as follows:

$$y = \varphi x^\alpha \qquad \text{EQN. 1,}$$

where φ represents an initial value of growth or decay, α is the growth or decay rate, with a positive value indicating an exponential growth and a negative value indicating a decay. FIG. 11 shows exemplary exponential growth and decay curves using EQN. 1 and extracted from the denoised data of FIG. 4, showing as examples growth and decay for $S_1$ and $S_2$ of the second 1100, third 1102, sixth 1104, and seventh 1106 cardiac cycles.

Summary of Extracted Features

Upon determining these features, a mathematical model is built, to calculate the systolic and diastolic BP based on the directly measured heart sounds, which may be implemented on a computer readable storage medium.

Table 1 lists a total of 13 parameters that are available for use in the disclosed mathematical model for calculating BP.

TABLE 1

Summary of the extracted features from the measured heart sounds.

| Name | Unit | Description |
| --- | --- | --- |
| HR | Bpm | Heart rate |
| $t_{s1}$ | Ms | $S_1$ duration |
| $t_{s2}$ | Ms | $S_2$ duration |
| $t_d$ | Ms | Diastole duration |
| $t_s$ | Ms | Systole duration |
| $\alpha_{ins1}$ | Dimensionless | $S_1$ growth constant |
| $\varphi_{ins1}$ | Dimensionless | $S_1$ growth initial value |
| $\alpha_{des1}$ | Dimensionless | $S_1$ decay constant |
| $\varphi_{des1}$ | Dimensionless | $S_1$ decay initial value |
| $\alpha_{ins2}$ | Dimensionless | $S_2$ growth constant |
| $\varphi_{ins2}$ | Dimensionless | $S_2$ growth initial value |
| $\alpha_{des2}$ | Dimensionless | $S_2$ decay constant |
| $\varphi_{des2}$ | Dimensionless | $S_2$ decay initial value |

Note that the diastolic duration $t_d$ is linked to the heart rate and the systolic duration $t_s$ by the following formulation:

$$t_d = 1/HR - t_s; \quad \text{EQN. 2.}$$

Using EQN. 2, the total number of parameters in the disclosed mathematical model is reduced to 12.

Mathematical Model

Figure 12:
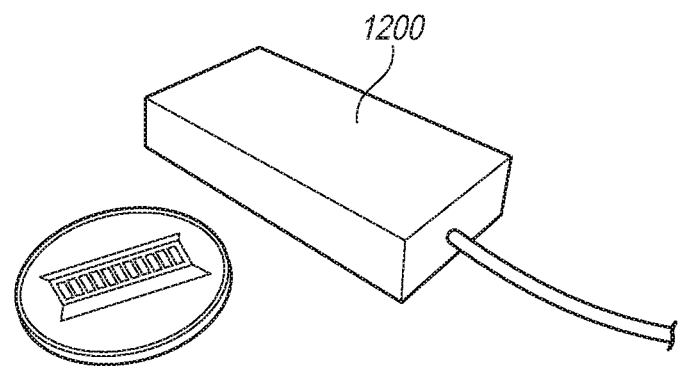
FIG. 12 shows an exemplary sensor.

The disclosed method used four groups of patients without abnormal heart diseases. FIG. 12 shows an exemplary sensor 1200 (having an accelerometer with decoupled piezoelectric layer) used for the disclosed method, and as may be used in the disclosed system. Sensor 1200 was taped on the chest of each patient to measure heart rates under different conditions: 1) sitting; 2) standing; 3) after exercises; and 4) after hyperventilation. The systolic and diastolic BP were measured using cuff/stethoscope under these conditions as benchmark data. Table 2 displays the measured data for four groups under four conditions.

TABLE 2

Summary of the Clinical data that were used to establish and validation of the proposed computer mode.

| Patient No. | Collection Conditions* | Sys, Pressure (mmHg) | Dias, Pressure (mmHg) | Heart rate bpm |
| --- | --- | --- | --- | --- |
| 1 | Hyp. | 134 | 65 | 130 |
|   | St. | 141 | 62 | 110 |
|   | Sit. | 145 | 71 | 92 |
|   | Rec. 1 | 146 | 58 | 125 |
|   | Rec. 2 | 144 | 61 | 125 |
| 2 | Sit. | 122 | 82 | 121 |
|   | Sit. | 128 | 71 | 93 |
|   | St. | 135 | 80 | 97 |
|   | St. | 136 | 83 | 103 |
|   | Sit. | 143 | 68 | 153 |
|   | Sit. | 146 | 67 | 130 |
| 3 | Sit. | 127 | 66 | 81 |
|   | Sit. | 134 | 85 | 93 |
|   | St. | 141 | 69 | 96 |
|   | St. | 142 | 74 | 94 |
|   | Sit. | 146 | 77 | 106 |
|   | Sit. | 157 | 65 | 108 |
| 4 | St. | 118 | 81 | 89 |
|   | Sit. | 124 | 76 | 76 |
|   | Hyp. | 129 | 76 | 100 |
|   | Rec. 1 | 132 | 66 | 122 |
|   | Rec. 2 | 151 | 82 | 144 |

*Hyp. Means that the data are collected after hyperventilation.
*St. means that patient was standing.
*Sit. Means that patient was sitting.
*Rec. means that patient was in recovery after excise.

Figure 13:
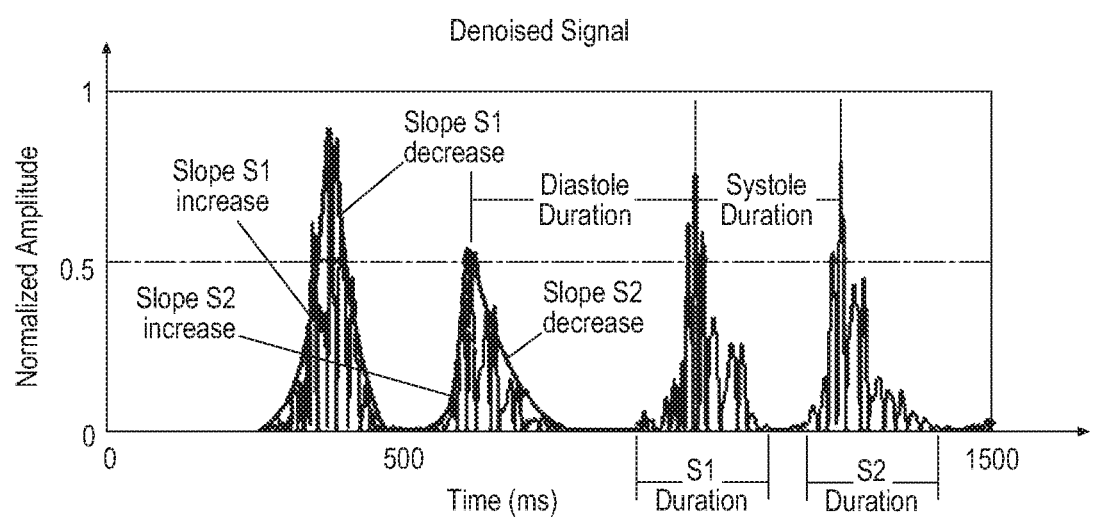
FIG. 13 shows corresponding slope increases and decreases for exemplary S1 and S2 data.

The mathematical model developed in this study can be summarized in the following formulations:

$$P_{sys} = 289 - 0.6 t_{s1} - 0.01 t_s - 0.9 \alpha_{ins1} - 13.3 \varphi_{ins1} + 1.44 \alpha_{des1} - 9.02 \varphi_{des1} - \alpha_{des2} + 5.1 \varphi_{des2}; \quad \text{EQN. 3,}$$

$$P_{dias} = -34.735 - 0.576 HR - 0.305 t_{s2} - 0.193 t_s + 9.064 \varphi_{des1} - 0.584 \alpha_{ins2} - 8.162 \varphi_{ins2}; \quad \text{EQN. 4,}$$

where EQN. 3 and EQN 4 depict systolic and diastolic BP, respectively, and the parameters involved in the equations are defined in Table 1. The coefficients associated with these parameters were obtained using known multiple regression analyses to ensure proper statistical merits of the systolic and diastolic BP. FIG. 13 shows, merely for illustration purposes, the corresponding slope increases and decreases for exemplary $S_1$ and $S_2$ data, as well as an illustration of $S_1$ and $S_2$ durations, corresponding to the various predictors according to the disclosure.

Figure 14:
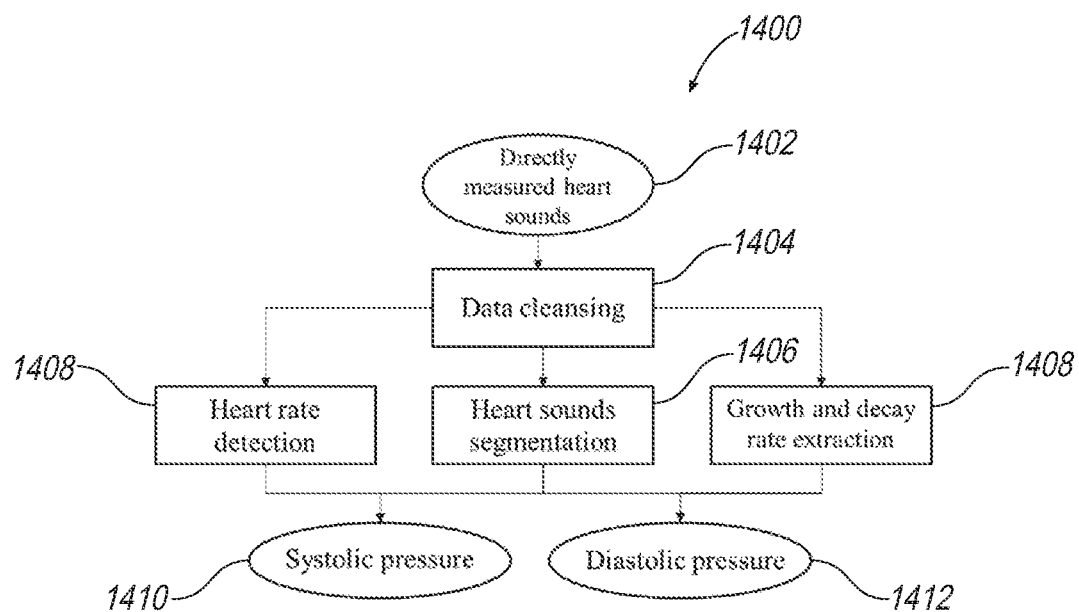
FIG. 14 illustrates an exemplary flowchart of the disclosed mathematical model.

FIG. 14 illustrates an exemplary flowchart 1400 of the disclosed mathematical model, summarizing the aforementioned steps. Input data are the heart sounds measured from the chest of a patient at step 1402. These data are cleansed at step 1404, including denoising first to ensure that that interfering signals, such as random background noise during measurements, lung sounds, etc. are eliminated. Next, $S_1$ and $S_2$ sounds are segmented 1406 and the heart rate is determined 1408, followed by the extraction of various features 1408 associated with $S_1$ and $S_2$ sounds, which are described mathematically and as summarized in Table 3.

Note that the feature extraction processes are performed by comparing P-values, using known regression results. Typically, P-values larger than 0.05 imply that this particular parameter is not statistically significant, designated in Tables 4 and 5 as N/A. In other words, the changes of the corresponding parameter are not correlated well with those of the desired output. Finally, EQNS. 3 and 4 are utilized to calculate the systolic and diastolic BP values, 1410, 1412. It is contemplated, however, that other applications of the disclosed method may include these predictors as statistically significant, and thus according to the disclosure EQNS. 3 and 4 may be generated using parameters that are deemed to be statistically significant, such as by having P-values less than 0.05. Further, although statistical significance, for the purpose of the disclosed example, is described as a P-value of less than 0.05, it is contemplated that such significance (or lack thereof) may be determined using a different P-value for cutoff, or an entirely different statistical approach to conduct the regression analysis.

arterial transducer may have errors of 7.5 mm HG or more resulting from: 1) an inaccurate transducer level, or 2) regular zeroing and/or flushing for accurate readings, as examples.

TABLE 3

Parameterization of a linear regression model for calculating the systolic blood pressure.

| Regression Statistics | | Predictor | Model with 12 predictors | | Model with feature selection | |
|---|---|---|---|---|---|---|
| | | | Standard Error | P-value | Standard Error | P-value |
| Model with 12 predictors | | HR | 0.183 | 0.228 | N/A | N/A |
| | | $t_{s1}$ | 0.241 | 0.030 | 0.090 | <0.01 |
| Statistics | 0.981 | $t_{s2}$ | 0.182 | 0.414 | N/A | N/A |
| R Square | 0.962 | $t_s$ | 0.002 | 0.021 | 0.002 | <0.01 |
| Adjusted R Square | 0.897 | $\alpha_{ins1}$ | 0.600 | 0.170 | 0.274 | <0.01 |
| Standard Error | 3.139 | $\varphi_{ins1}$ | 5.733 | 0.088 | 2.936 | <0.01 |
| Model with feature selection | | $\alpha_{ins1}$ | 0.364 | <0.01 | 0.168 | <0.01 |
| | | $\varphi_{ins1}$ | 2.984 | 0.014 | 2.730 | <0.01 |
| Statistics | 0.968 | $\alpha_{ins2}$ | 0.184 | 0.579 | N/A | N/A |
| R Square | 0.938 | $\varphi_{ins2}$ | 4.576 | 0.887 | N/A | N/A |
| Adjusted R Square | 0.894 | $\alpha_{ins2}$ | 0.382 | 0.099 | 0.237 | <0.01 |
| Standard Error | 3.170 | $\varphi_{ins2}$ | 5.650 | 0.177 | 2.268 | <0.01 |

TABLE 4

Parameterization of a linear regression model for calculating the diastolic blood pressure.

| Regression Statistics | | Predictor | Model with 12 predictors | | Model with feature selection | |
|---|---|---|---|---|---|---|
| | | | Standard Error | P-value | Standard Error | P-value |
| Model with 12 predictors | | HR | 0.697 | 0.142 | 0.215 | 0.019 |
| | | $t_{s1}$ | 0.416 | 0.954 | N/A | N/A |
| Statistics | 0.931 | $t_{s2}$ | 0.267 | 0.120 | 0.114 | 0.019 |
| R Square | 0.867 | $t_s$ | 0.219 | 0.422 | 0.109 | <0.01 |
| Adjusted R Square | 0.578 | $\alpha_{ins1}$ | 0.840 | 0.381 | N/A | N/A |
| Standard Error | 5.198 | $\varphi_{ins1}$ | 10.070 | 0.947 | N/A | N/A |
| Model with feature selection | | $\alpha_{ins1}$ | 0.781 | 0.998 | N/A | N/A |
| | | $\varphi_{ins1}$ | 6.258 | 0.130 | 4.360 | 0.048 |
| Statistics | 0.841 | $\alpha_{ins2}$ | 0.960 | 0.425 | 0.206 | 0.014 |
| R Square | 0.707 | $\varphi_{ins2}$ | 10.464 | 0.446 | 2.686 | <0.01 |
| Adjusted R Square | 0.571 | $\alpha_{ins2}$ | 0.659 | 0.484 | N/A | N/A |
| Standard Error | 5.24 | $\varphi_{ins2}$ | 9.714 | 0.444 | N/A | N/A |

Table 3 shows that among the 12 parameters for the systolic pressure regression model, parameters HR, ts2, $\alpha_{ins2}$ and $\varphi_{ins2}$ are not statistically significant because their P-values all greater than the threshold of 0.05. Consequently, these parameters were removed them from the mathematical model and a regression analysis is redone to ensure that P-values are satisfactory. The same processes are also carried out for diastolic pressure calculations and the results are shown in Table 4.

Figure 15:
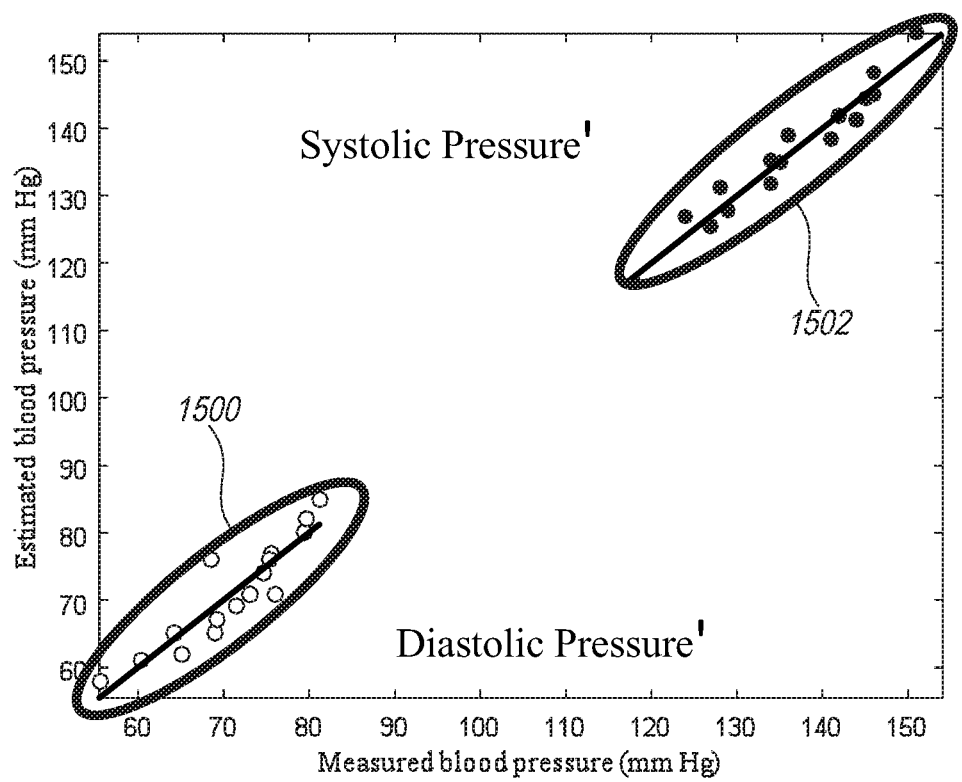
FIG. 15 summarizes calculated systolic and diastolic BP values obtained using the disclosed method.

FIG. 15 summarizes the calculated systolic and diastolic BP values, and provides an opportunity to compare measured BP with that determined using the disclosed method. Note that all the calculated values, i.e., diastolic pressure dots 1500 and systolic pressure dots 1502 fall on a straight line of ∠45°, which means that measured and calculated systolic and diastolic BP values have a high correlation. Note that this ∠45° line implies that the rate of increases in measured BP is effectively the same as that in calculated ones.

As a reference, the Gold standard in measuring BP by using an invasive arterial cannulation and placing an intra- Accordingly, a mathematical model is disclosed to determine the systolic and diastolic BP based on the heart sound signals measured directly on the chests of patients without abnormal heart diseases.

The measured heart sounds were first denoised to eliminate random background noise and interfering signals such as lung sounds. Next, an averaged heart rate was estimated, $S_1$ and $S_2$ sounds were separated, and features involved in $S_1$ and $S_2$ sounds were extracted. These features were then used in a semi-empirical computer model to calculate the systolic and diastolic BP, and were compared with the benchmark data obtained by using conventional cuff/stethoscope method. Satisfactory agreements between the calculated and measured data were obtained.

Furthermore, disclosed herein is a theoretical foundation for the newly developed methodology that enables the prediction of blood pressures based on the heart sounds measured directly on the chest of a patient.

The following portion of the disclosure presents a theoretical foundation for the disclosed methodology that enables the prediction of blood pressures based on the heart sounds measured directly on the chest of a patient. One aspect of this methodology is the separation of heart sounds into first heart sound and second heart sound, from which components attributable to four heart valves, i.e.: mitral; tricuspid; aortic; and pulmonary valve-closure sounds are separated.

Because human physiology and anatomy can vary among people and are unknown a priori, such separation is called blind source separation. Moreover, the sources locations, their surroundings and boundary conditions are unspecified. Consequently, it is difficult to obtain an exact separation of signals. To circumvent this difficulty, the point source separation method is extended in this disclosure to an inhomogeneous fluid medium, and further combined with iteration schemes to search for approximate source locations and signal propagation speed. Once these are accomplished, the signals emitted from individual sources are separated by deconvoluting mixed signals with respect to the identified sources.

Blind Source Separation (BSS) aims at separating individual signals from a set of mixed data collected by multiple sensors. Applications of BSS have been found in almost all fields including analyzing bio-medical signals, speeches, machine health monitoring, radio communications, and others. In particular, in bio-acoustical fields, BSS have been used to improve speech recognition in bilateral cochlear implant patients, to analyze functional magnetic resonance imaging (fMRI) data, electroencephalography (EEG) signals, etc. In analyzing acoustic signals, locating and separating noise sources via multi-channel microphones is an effective approach for both airborne and structural-born noise problems. BSS also enables one to extract target vibration signals generated by a specific mechanical machine from directly measured data that have been contaminated by interfering signals emitted from other machines, which can be very helpful for machine health monitoring and diagnosis.

BSS has been implemented through advanced signal processing techniques, which includes independent component analysis (ICA), principal component analysis (PCA), non-negative matrix factorization method, stationary subspace analysis, common spatial pattern method, etc.

According to this disclosure, BSS is implemented using a modified point source separation (PSS) method. One difference between PSS and ICA and PCA is that the former can reveal explicit correlations between the separated signals and their respective sources and separated results are definitive and stable; whereas the latter cannot tell which separated signals are from which sources, and results can change from one run to another. That is, in PSS separations of source signals are performed through deconvolution processes with respect to the source locations. In the original PSS approach, the locations of individual sources are calculated via a time difference of arrival (TDOA) based algorithms. Using this approach, not only can source locations be determined, but also their signals may be extracted. One shortcoming of this hybrid approach, though, is that it typically works for a free field only. In practice, a true free field is usually not present because there are always boundary surfaces and obstacles in the test area, and because the acoustic characteristics of these boundary surfaces and obstacles are unknown a priori. Under these circumstances, analytic solutions are not available, and thus only approximate solutions are obtained.

One goal of this disclosure is to provide a theoretical foundation for developing a practical yet very effective methodology that enables one to estimate blood pressures based on the heart sounds measured directly on a patient's chest. Using this semi-empirical approach, a BSS can be performed in a highly non-ideal environment, which involves an inhomogeneous medium with an unspecified number of obstacles and unknown boundary surfaces.

Point Source Separation (PSS) Method

The essence of PSS is outlined below. The following is based on an assumption where sources are of negligible dimensions and the medium is unbounded, homogenous, and quiescent. Accordingly, the acoustic pressure anywhere can be written as a superposition of contributions from all point sources by using the free-space Green's function:

$$p(x_m, t) = \sum_{n=1}^{N} \frac{s(x_n, t - R_{mn}/c)}{R_{mn}};$$ EQN. 5, where $p(x_m, t)$ indicates the acoustic pressure at the $m^{th}$ sensor $x_m$, which is the sum of contributions from a number of incoherent point sources $s(xn, t-Rmn/c)$ located at $x_n$, n=1 to N. Note that $p(x_m, t)$ is identically zero when t<0, and $R_{mn}$ is the distance between the $n^{th}$ source and $m^{th}$ sensor, and c is the speed of sound.

The Fourier transformed acoustic pressure p $(x_m, \omega)$ is given by:

$$p(x_m, \omega) = \sum_{n=1}^{N} G(x_m | x_n; \omega) S(x_n, \omega);$$ EQN. 6, where $G(x_m|x_n;\omega) = e^{ikR_{mn}}/R_{mn}$ is commonly referred to as the free-space Green's function. In matrix form, EQN. (6) can be rewritten as:

$$\{P(x_m,\omega)\}_{M\times 1} = [G(x_m|x_n;\omega)]_{M\times N} \{S(x_n,\omega)\}_{N\times 1};$$ EQN. 7, The source signals $\{S(x_n,\omega)\}_{N\times 1}$ can be determined by taking a pseudo inversion of EQN 7:

$$\{S(x_n,\omega)\}_{N\times 1} = [G(x_n|x_m; \omega)]_{N\times M}^{\dagger} \{P(x_m,\omega)\}_{M\times 1};$$ EQN. 8, where a superscript † implies a pseudo inversion of a rectangular matrix defined as:

$$[G(x_n|x_m);\omega]_{N\times M}^{\dagger} = \{[G(x_m|x_n;\omega)]_{N\times M}^{H}[G(x_m|x_n;\omega)]_{M\times N}\}^{-1} \times [G(x_m|x_m;\omega)]_{N\times M}^{H};$$ EQN. 9, where a superscript H implies a Hermitian (conjugate transposition) of a complex matrix.

EQN. 8 provides an exact solution when M=N, a least-square solution when M>N. When M<N, a solution may still be obtained by using singular value decomposition. The accuracy may be reduced, however, since not enough information is collected. In any event, the separated signals may be written due to the nth source as:

$$S(x_n, \omega) = \sum_{m=1}^{M} G^{\dagger}(x_n | x_m; \omega) P(x_m, \omega);$$ EQN. 10.

The corresponding time-domain signals s(xn, t) can now be obtained by taking the inverse Fourier transform of EQN. 10:

$$S(x_n, t) = \sum_{n=1}^{N} \int_{-\infty}^{\infty} g^{\dagger}(x_n | x_m; t') p(x_m, t-t') dt';$$ EQN. 11, where $g^\dagger(x_n|x_m; t')$ indicates the inverse Fourier transform of $G^\dagger(x_n|x_m; \omega)$:

$$g^\dagger(x_n|x_m;t') = \frac{1}{2\pi}\int_{-\infty}^{\infty} G^\dagger(x_n|x_m;\omega)e^{-i\omega t'}d\omega; \quad \text{EQN. 12,}$$

where $G^\dagger(x_n|x_m; \omega)$ depicts the element of the pseudo inverse matrix given by EQN. 9.

Adaptive PSS

Limitations of PSS

EQN. 11 can be rewritten in a standard convolution format:

$$s(x_n,t) = \sum_{n=1}^{N} g^\dagger(x_n|x_m;t') * p(x_m, t-t'); \quad \text{EQN. 13.}$$

From the above equation, it is seen that the original PSS is accomplished by deconvolving the influence function $g^\dagger(xn|xm; t)$ with respect to measured acoustic pressure signals.

By definition, the influence function involves distances between the $n^{th}$ source $x_n$ and $m^{th}$ measurement point $x_m$, and propagating speed c. In the original PSS method, the fluid medium is homogeneous, unbounded and quiescent, the speed of sound is given, and the distances $R_{mn}$ between the $n^{th}$ point source and $m^{th}$ sensor can be calculated using the spherical spreading law and triangulation algorithms.

According to this disclosure, the PSS approach is extended to an inhomogeneous and confined fluid medium without prior knowledge of the propagation speed. It is emphasized that under this condition, there is no analytic solution in general. Accordingly, an optimal and approximate solution is sought. The accuracy in source localization may be compromised, especially when there are non-negligible sound reflections, reverberations, and presence of random background noise. These factors can cause a reduction of signal-to-noise ratio (SNR), making BSS more challenging.

Impact of Source Localization and Propagation Speed Errors on Signal Separation

Following is an examination of the accuracy in source localization in an adaptive algorithm for an adaptive PSS method. To this end, error analyses are conducted to reveal correlations of the source localization errors and propagation speed errors on source separation results. One aspect is to establish the correct influence function, which is unspecified. Thus, in this disclosure, an idealized influence function plus errors is started with, and an iteration algorithm is used to minimize errors involved in this influence function.

EQN. 10 shows that the separated signals in the frequency domain are expressible in a matrix form as:

$$\{C(x_n,\omega)\}_{N\times 1}=[G'(x_n|x_m|\omega)]_{N\times M}^\dagger \{P(x_n,\omega)\}_{M\times 1}; \quad \text{EQN. 14,}$$

where $[G'(x_n|x_m; \omega)]_{N\times M}^\dagger$ indicates a pseudo inversion of an incorrect influence function, $\{P(x_m, \omega)\}_{M\times 1}$ represent the input data, and $\{C(x_n, \omega)\}_{N\times 1}$ are the resultant separated signals. For simplicity, we assume that the input data $\{P(x_m, \omega)\}_{M\times 1}$ are correct. Hence, the errors involved in separated signals are caused by the use of an incorrect influence function.

To examine the difference between the true source signals and separated signals, EQN. 10 is inverted to express $\{P(x_m, \omega)\}_{M\times 1}$ in terms of $[G'(x_n|x_m; \omega)]_{M\times N}$ and $\{C(x_n, \omega)\}_{N\times 1}$, and substituted into EQN. 10:

$$\{S(x_n,\omega)\}_{N\times 1}=[A(x_n|x_m;\omega)]_{N\times N}\{C(x_n,\omega)\}_{N\times 1}; \quad \text{EQN. 15,}$$

where the square matrix $[A(x_n|x_m; \omega)]_{N\times N}$ is given by:

$$[A(x_n|x_m;\omega)]_{N\times N}=[G(x_n|x_m;\omega)]_{N\times M}^\dagger[G'(x_n|x_m;\omega)]_{M\times N}; \quad \text{EQN. 16.}$$

It is noted that errors contained in $\{C(x_n, \omega)\}_{N\times 1}$ are cancelled by those contained in $[A(x_n|x_m; \omega)]_{N\times N}$ on the right side of EQN. 15. Hence, the signals $\{S(x_n, \omega)\}_{N\times 1}$ on the left side of EQN. 15 are correct. The difference between the true signals $\{S(x_n, \omega)\}_{N\times 1}$ and the separated signals $\{C(x_n, \omega)\}_{N\times 1}$ can be written as a column vector:

$$\{e(x_n,\omega)\}_{N\times 1}=\{[A(x_n|x_m;\omega)]_{N\times N}-[I]_{N\times N}\}\{C(x_n,\omega)\}_{n\times 1}; \quad \text{EQN. 17.}$$

EQN. 17 indicates that if the square matrix $[A(x_n|x_m; \omega)]_{N\times N}$ is a unitary matrix, there is no difference between the separated signals and true signals, which means that the influence matrices $[G'(x_n|x_m; \omega)]_{M\times N}$ is cancelled by a pseudo inversion $[G'(x_n|x_m; \omega)]_{N\times M}^\dagger$. Thus, one goal is to minimize the differences between $[A(x_n|x_m; \omega)]_{N\times N}$ and the unitary matrix.

To this end, a mean-squared estimator is defined and its value minimized. Mathematically, such a process is expressible as:

$$R_{ee}=E[ee^T]=AR_{CC}A^T-AR_{CC}-R_{CC}A^T+R_{CC}=\text{minimum}; \quad \text{EQN. 18.}$$

Note that a "perfect" separation also leads to the estimation error, which is a linear transformation of C, but uncorrelated to C. Therefore, the following constraint is applied:

$$R_{eC}=E[eC^T]=E[(AC-C)C^T]=AR_{CC}-R_{CC}=0; \quad \text{EQN. 19.}$$

The condition $R_{eC}=0$ implies that:

$$A_{opt}=R_{CC}R_{CC}^{-1}=E_{N\times N}; \quad \text{EQN. 20,}$$

where $A_{opt}$ represents the optimal square matrix $\lfloor A(xn|xm; \omega)\rfloor N\times N$, which can lead to the best s1eparation of source signals. This is because if $A_{opt}$ is substituted to EQN. 18, the residue $R_{ee}$ is identically zero:

$$R_{ee}^{min}=R_{CC}-R_{CC}-R_{CC}+R_{CC}=0; \quad \text{EQN. 21}$$

Other choices of A will lead to a larger residue, and a bigger difference between the true signals and separated ones.

To acquire a better understanding of the impact of A on the mean-squared estimation error, A is replaced by $A_{opt}$ plus a small deviation $\Delta A$:

$$A=A_{opt}+\Delta A=E+\Delta A; \quad \text{EQN. 22.}$$

Substituting EQN. 22 into EQN. 18 results in:

$$R_{ee}=\Delta A R_{CC}\Delta A^T=\Delta A(E+\Delta A)^{-1}R_{SS}[(E+\Delta A)^{-1}]^T\Delta A^T; \quad \text{EQN. 23;}$$

where $R_{SS}$ implies the auto-correlation matrix of source signals. Because sources are assumed uncorrelated, the off-diagonal terms in $R_{S_iS_j}$, $i \neq j$, are zero and the normalized diagonal terms $R_{S_iS_i}\equiv 1$. Hence, separation errors $R_{ee}$ are indeed introduced by deviations $\Delta A$.

Note that the mean-squared separation error $R_{ee}$ cannot be calculated directly, because true source signals S and exact matrix A are unknown at a priori. The information available is the trial separated signal $\{C(x_n, \omega)\}_{N\times 1}$ with respect to a trial operator A.

Accordingly, the auto-correlation of $\{C(x_n, \omega)\}_{N\times 1}$ can be written as:

$$R_{CC} = \begin{bmatrix} R_{C_1C_1} & R_{C_1C_2} & \cdots & R_{C_1C_n} \\ R_{C_2C_1} & R_{C_2C_2} & \cdots & R_{C_2C_n} \\ \vdots & \vdots & \ddots & \vdots \\ R_{C_nC_1} & R_{C_nC_2} & \cdots & R_{C_nC_n} \end{bmatrix} = \qquad \text{EQN. 24.}$$

$$(E+\Delta A)^{-1}_{N\times N} \begin{bmatrix} R_{S_1S_1} & R_{S_1S_2} & \cdots & R_{S_1S_n} \\ R_{S_2S_1} & R_{S_2S_2} & \cdots & R_{S_2S_n} \\ \vdots & \vdots & \ddots & \vdots \\ R_{S_nS_1} & R_{S_nS_2} & \cdots & R_{S_nS_n} \end{bmatrix} [(E+\Delta A)^{-1}]^H_{N\times N};$$

Note that the off-diagonal terms in EQN. 24 represents cross correlations of signals, while the diagonal terms signify auto correlations of signals. Because sources are assumed uncorrelated, all off-diagonal terms should be zero theoretically. Accordingly, for perfectly separated signals $R_{CC}$ is an identity matrix:

$$R_{C_iC_j} = \begin{cases} 0 & i \neq j \\ 1 & i = j_1 \end{cases}; \qquad \text{EQN. 25.}$$

Based on this concept, the PSS algorithm is used repeatedly with respect to an operator matrix A, until the off-diagonal terms of $R_{CC}$ are negligibly small. It is emphasized that, in actuality, fully uncorrelated sources might not exist. However, an optimal operator A can still be identified by minimizing off-diagonal terms in $R_{CC}$. In other words, a "wrong" influence function will have large values of off-diagonal terms in $R_{CC}$.

Thus, errors in source separation are mainly caused by the fact that the source locations and signal propagation speed are unspecified, and are therefore guessed. Such guesses can produce significant errors in source separation. Thus, one goal is to minimize the impacts of the errors involved in source localization and in guessing a signal propagation speed on resultant source separation, which is reflected in the presence of non-zero off-diagonal terms in $R_{CC}$.

Adaptive PSS Algorithm

An adaptive PSS is the original PSS supplemented by adaptive selections of source locations and propagation speed via the minimization process given by EQN. 18. Beginning with an assumption that there are N sources and M sensors, the number of off-diagonal terms of $R_{CC}$ to be minimized is given by:

$$\binom{N}{2} = \frac{N(N-1)\ldots(N-2+1)}{2\times(2-1)} = \frac{N!}{2(N-2)!}; \qquad \text{EQN. 26.}$$

The number of variables affecting the operator A is M×N+1. Each variable may vary over a wide range, making an adaptive PSS algorithm a very time-consuming process. For simplicity yet without losing generality, in the present disclosure it is considered to separate two target sources based on the input data collected from two sensors, saying M=2 and N=2. Thus, the one off-diagonal term is minimized in $R_{CC}$ and five unknown parameters are determined.

Note that in general, sensors are placed near target sources to enhance the signal to noise ratio, and sensor locations are typically specified. Use of an adaptive PSS algorithm to separate two sources includes the following three stages:

(1) Searching target sources around sensors;
(2) Determining signal propagation speed based on an initial best guess;
(3) Establishing an optimum influence matrix that will lead to the best separation of source signals.

Figure 16:
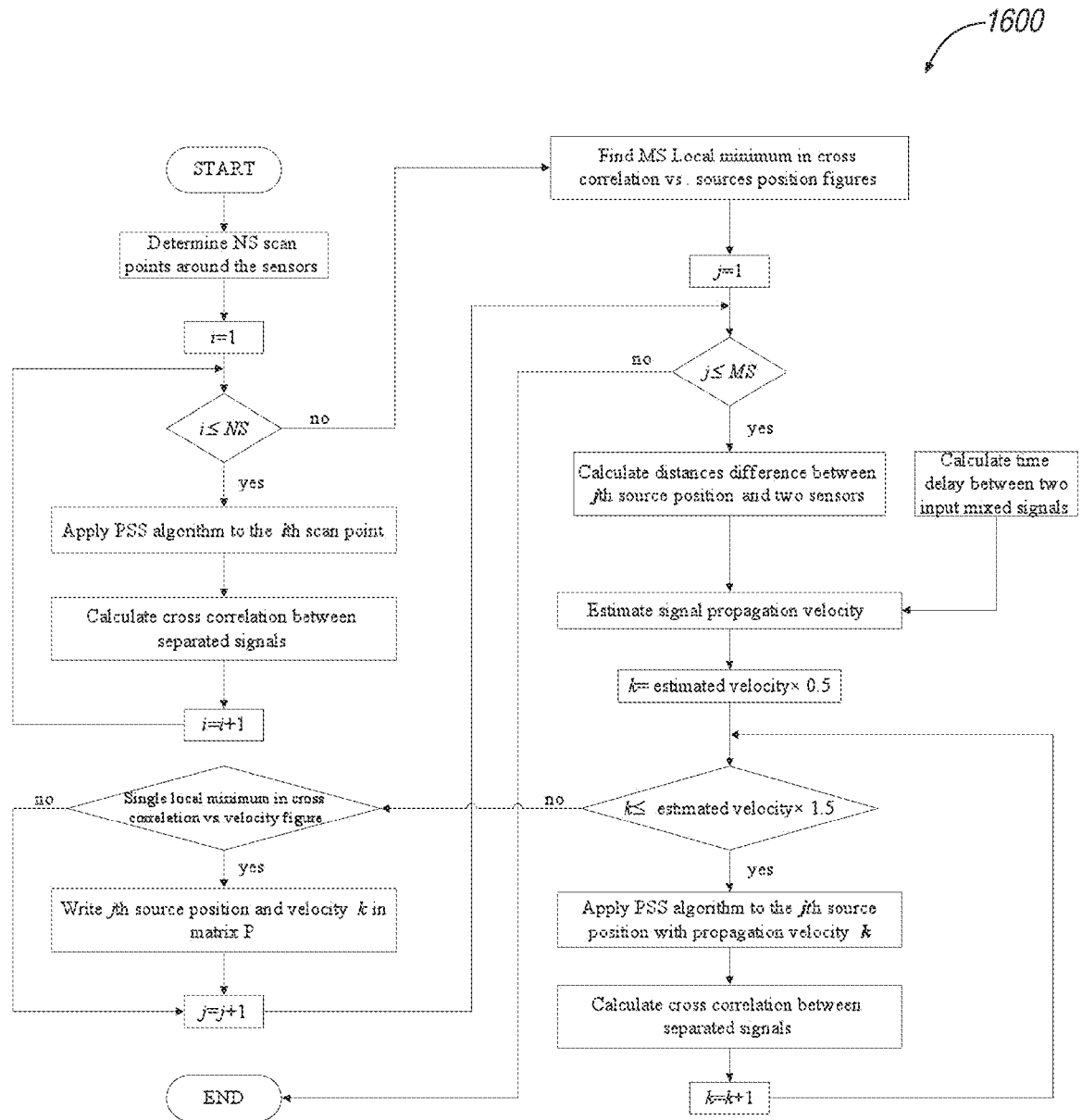
FIG. 16 illustrates a flowchart of the disclosed adaptive PSS algorithm.

FIG. 16 illustrates a flowchart 1600 of the disclosed adaptive PSS algorithm. First, PSS is applied to NS combinations of possible positions around two sensors, and find MS local minimum values in $R_{CC}$. The goal of this step is to reduce the number of trials as much as possible to facilitate the determination of propagation speed.

Figures 17, 18:
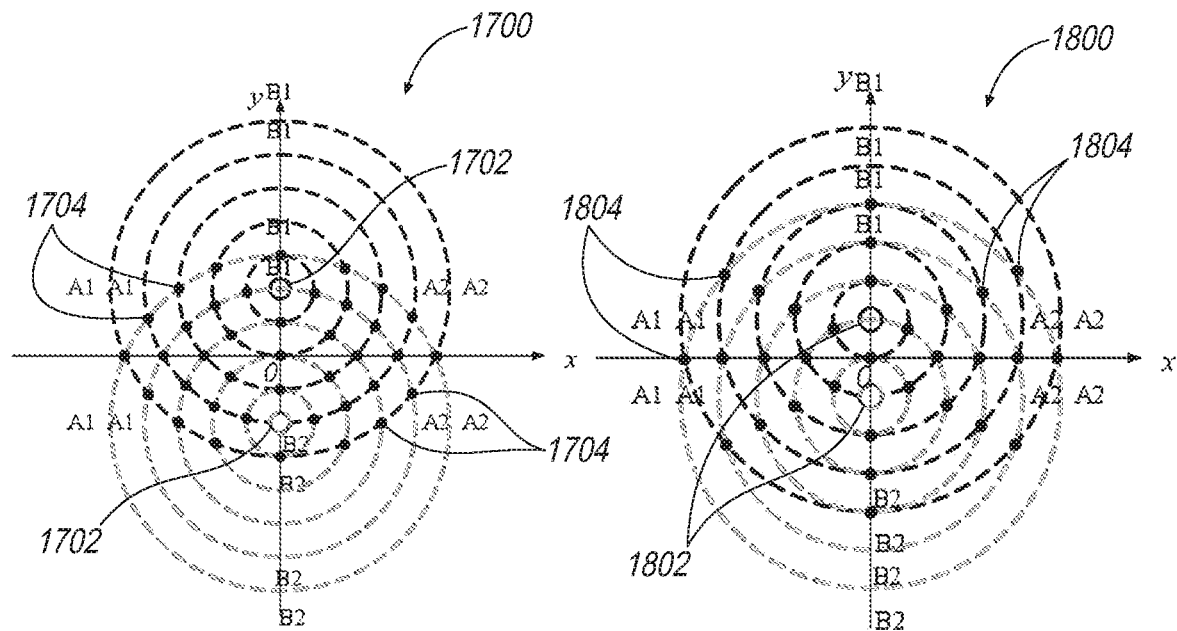
FIG. 17 illustrates one of two options that may be used to separate heart sounds emitted by four heart valves.
FIG. 18 illustrates another of two options that may be used to separate heart sounds emitted by four heart valves.

The paths of searches can be quite different depending on specific applications. For example, FIGS. 17 and 18 illustrate two options 1700, 1800 that may be used to separate heart sounds emitted by four heart valves, namely, mitral, tricuspid, aortic and pulmonary valve-closure sounds. In these figures, two big dots 1702, 1802 at the center represent sensors locations, and smaller dots around sensors 1704, 1804 are possible source locations. In each run of the PSS algorithm, possible locations are chosen for both sources. Thus, with a total 39 and 33 possible positions as shown in FIGS. 17 and 18, the number of possible source locations NS are 741 and 528, respectively.

In each run of source locations, the distances between sources and sensors are calculated. Time delay of signal traveling from one sensor to another is obtained by taking a cross correlation of signals measured at the sensors. Accordingly, the signal propagation speed can be calculated by dividing the time delay between these sensors by their relative distance.

Next, for each of those MS possible position combinations obtained from stage one, varying the signal propagating speed by ±50% of the approximation value and see whether there is a local minimum in $R_{CC}$. Recall from the previous error analyses, a wrong speed value always leads to a larger value of $R_{CC}$ for the separated results. Thus, the correct propagation speed can be selected that corresponds to the minimum value in $R_{CC}$.

Numerical Simulations

Figure 19:
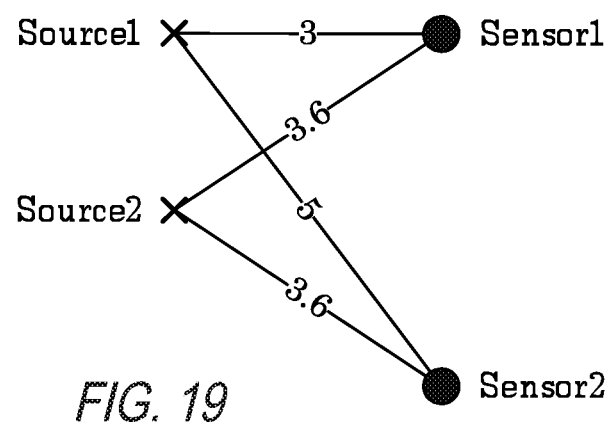
FIG. 19 illustrates an exemplary test configuration.

To verify the disclosed adaptive PSS algorithms, numerical simulations were conducted to separate two incoherent source signals by using two sensors. FIG. 19 illustrates the test configuration. Relative distances of sensors and sources are arbitrarily selected, with length in units of centimeters.

Figure 20:
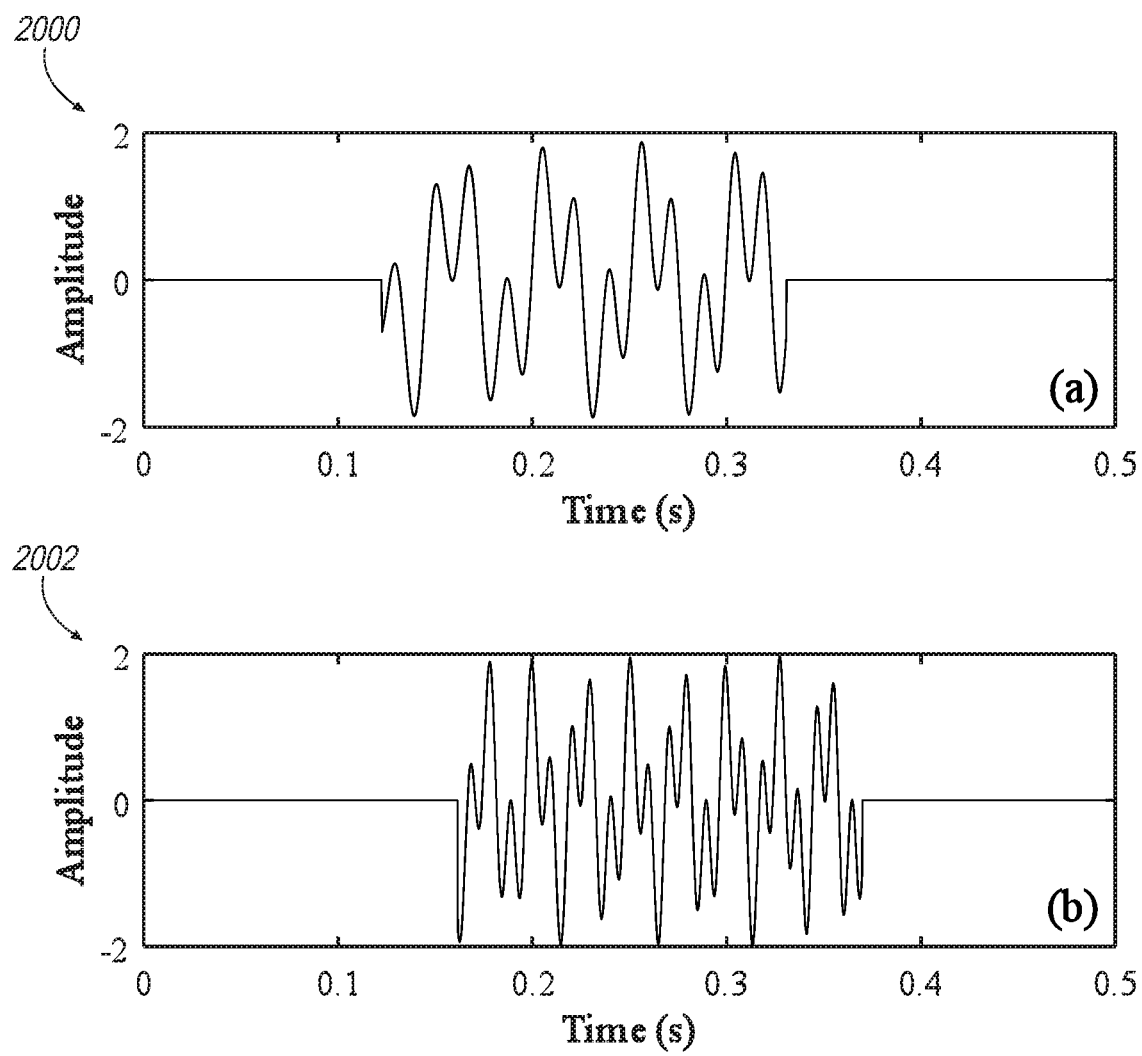
FIG. 20 shows arbitrarily chosen signals related to S1 and S2.

The signal propagation speed was initially set at c=409.6 cm/s resulting in $R_{11}$=3 cm, $R_{12}$=5 cm, $R_{21}$=3.6 cm and $R_{22}$=3.6 cm. The source signals were given in EQNS. 27 and 28, respectively, and their wave forms are demonstrated in FIG. 20 (showing arbitrarily chosen signals #1 [a] 2000 and #2 [b] 2002).

$$s_1(t) = \begin{cases} 0 & t \leq 0.125 \\ \sin(40\pi t) + 2\cos[(80\pi + 120\pi t)t] & 0.125 < t \leq 0.3125; \\ 0 & t > 0.3125 \end{cases} \qquad \text{EQN. 27;}$$

$$s_2(t) = \begin{cases} 0 & t \leq 0.1875 \\ \sin(80\pi t) + 2\cos[(120\pi + 160\pi t)t] & 0.1875 < t \leq 0.375; \\ 0 & t > 0.375 \end{cases} \qquad \text{EQN. 28.}$$

Figure 21:
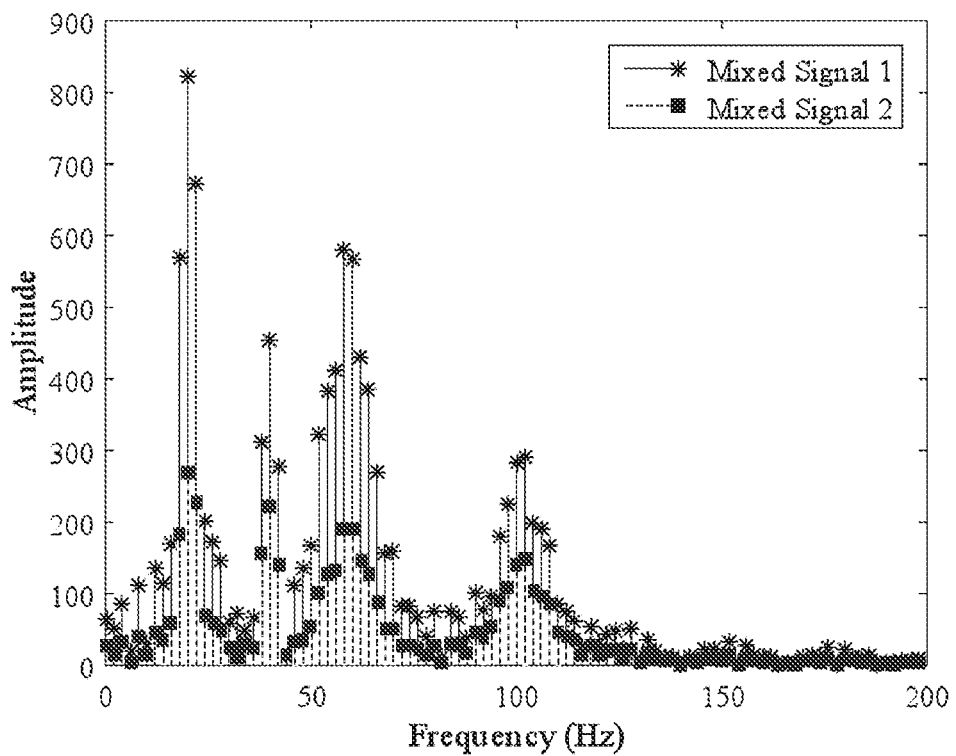
FIG. 21 shows a spectrum of measured mixed signals.
Figure 22:
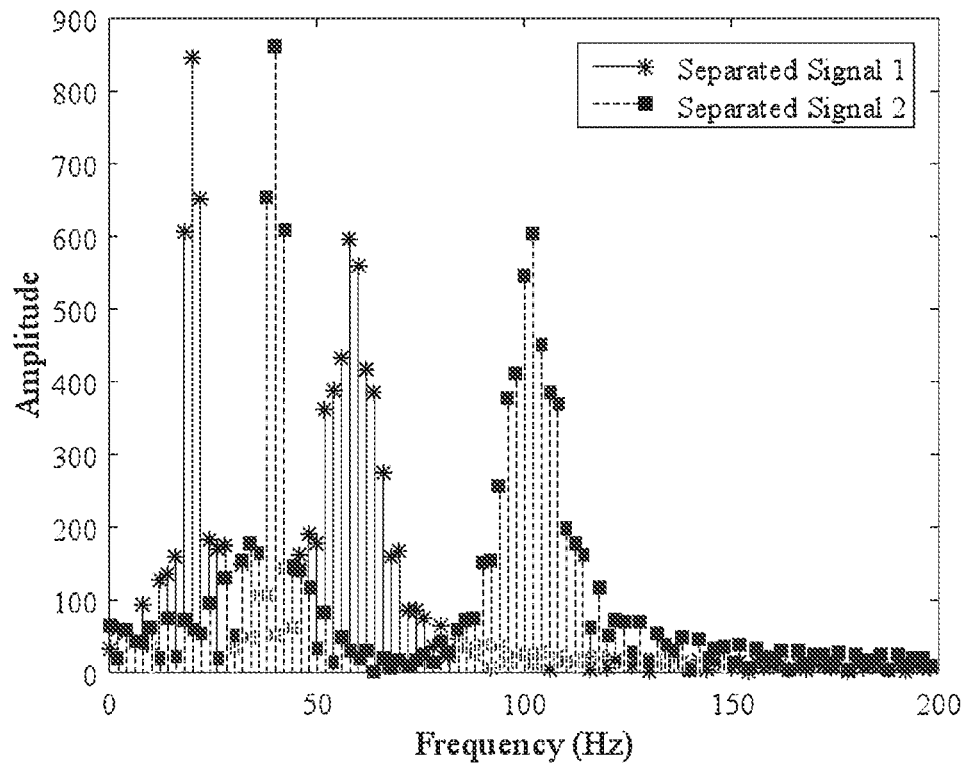
FIG. 22 shows a spectrum of separated signals.
Figure 23:
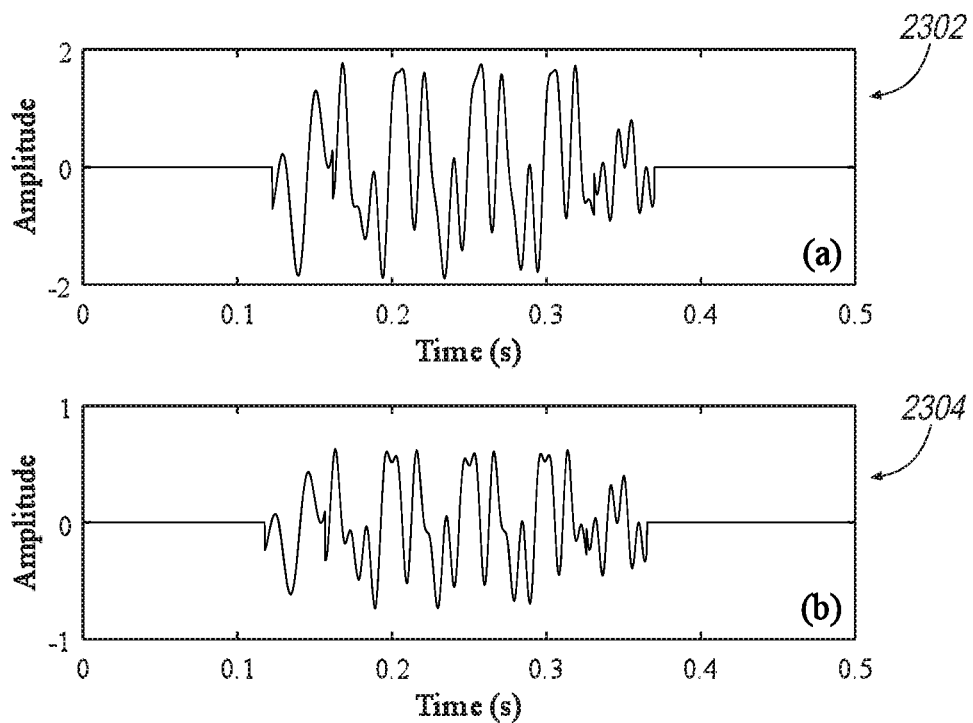
FIG. 23 shows measured time-domain mixed signals in Channel #1 and measured time-domain mixed signals in Channel #2.
Figure 24:
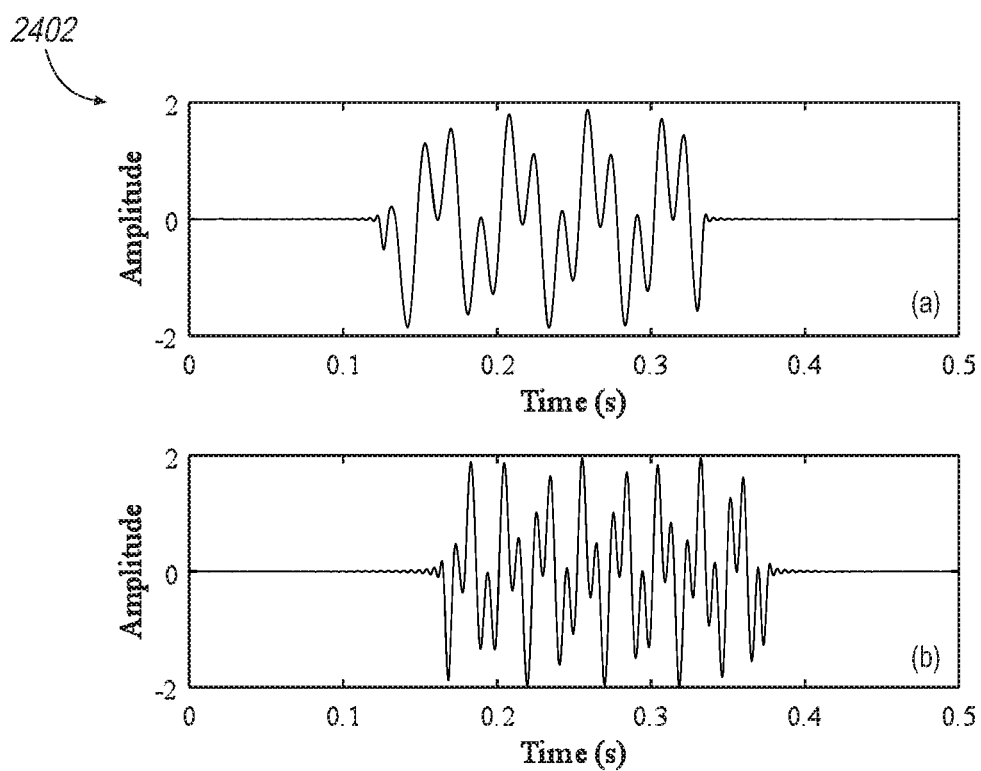
FIG. 24 shows separated source signals #1 and separated source signals #2.

It is noted that propagating speed, sensor, and source relative positions, and signals were arbitrarily chosen, and have no impact on source separation results. FIG. 21 shows a spectrum of measured mixed signals, and FIG. 22 shows a spectrum of separated signals. FIG. 23(a) 2302 shows measured time-domain mixed signals in Channel #1; FIG. 23(b) 2304(b) shows measured time-domain mixed signals in Channel #2; FIG. 24(a) 2402 shows separated source signals #1; and FIG. 24(b) 2404 shows separated source signals #2.

Thus, the PSS algorithm is effective when correct locations of sources and correct speed of signal are specified. Now, consider cases for which these parameters are not specified, and are therefore initially guessed. Without loss of generality, a propagation speed c=209.6 cm/s is used, in this example, which is about one-half of the correct value, and $R_{12}$=5.6 cm, which is 0.6 cm longer than the correct distance.

Figure 25:
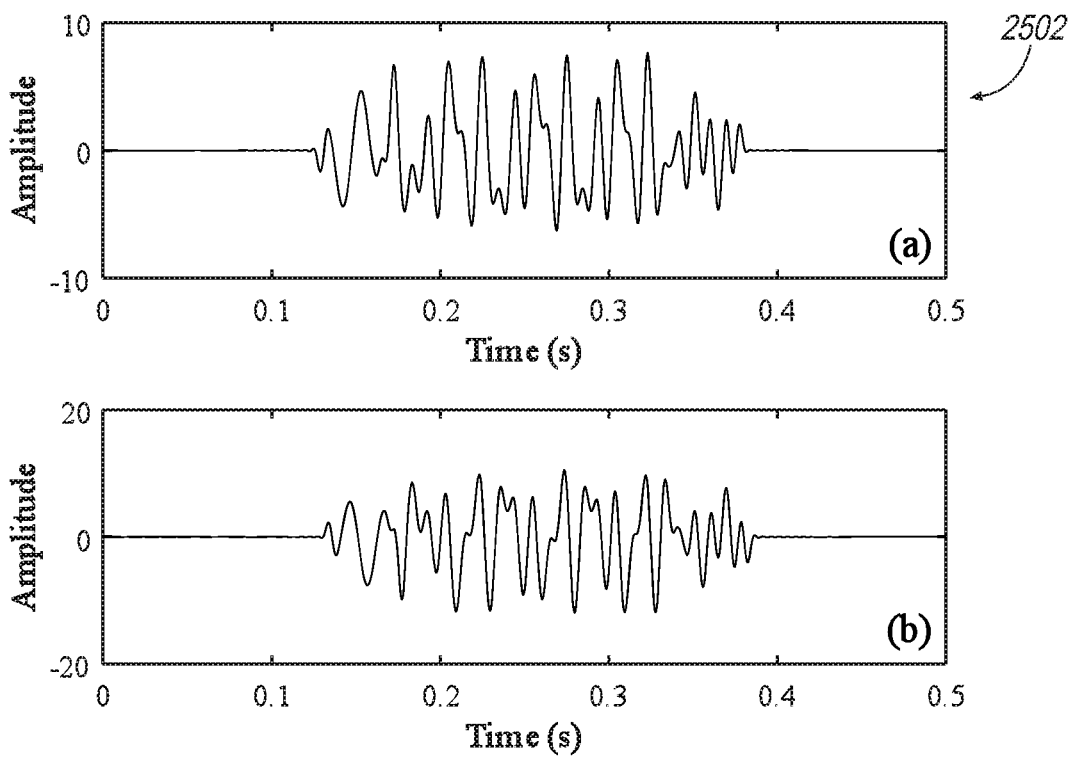
FIGS. 25 and 26 display that in both situations, source signals cannot be separated from each other.
Figure 26:
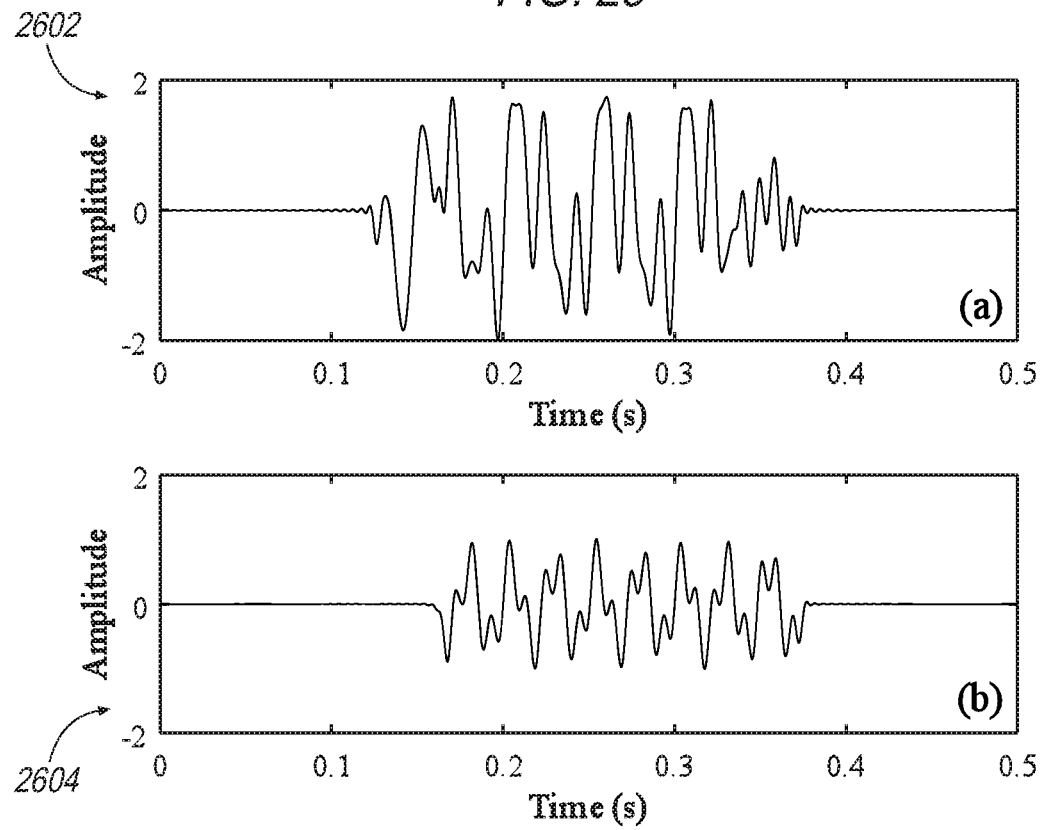

FIGS. 25 and 26 display that in both situations, source signals cannot be separated from each other. The maximum normalized cross-correlation values are 0.9779 and 0.9349, respectively, indicating that these signals are highly correlated. This example confirms that incorrect guesses of the propagating speed and source locations can lead to erroneous separation results. As discussed above, unsatisfactory separation results are due to the combined effects of incorrect input data on propagation speed and source locations, which have direct impacts on both amplitudes and phases of signals. That is, referring to FIGS. 25 and 26 having separated signals with c=209.6 cm/s, FIG. 25(a) 2502 shows separated source signal #1; and FIG. 25(b) (b) shows separated source signal #2, which are very different from the true signals.

Referring to FIGS. 26(a) and (b), separated signals are shown with $R_{12}$=5.6 cm, with FIG. 26(a) showing separated source signal #1; and FIG. 26(b) showing separated source signal #2, both being very different from the true signals.

The impact of propagation speed and source locations in is studied in further detail.

Effect of Signal Velocity

The disclosed PSS algorithm is mainly based on analyzing amplitude and phase variations during propagation. More specifically, the amplitudes are estimated by traveling distances and the phase information is calculated by traveling distances divided by propagation speed. Thus, errors in propagation speed will affect the phase estimation directly.

To examine the impact of propagation speed error on separation result, the speed is varied from 200 cm/s to 600 cm/s. The correct value is 409.6 cm/s, which is in the middle of this range. Note that there is no need to have the correct speed value in the middle of the search range. The reason for doing so is to make it easier to demonstrate the correct speed through an iteration scheme.

Figure 27:
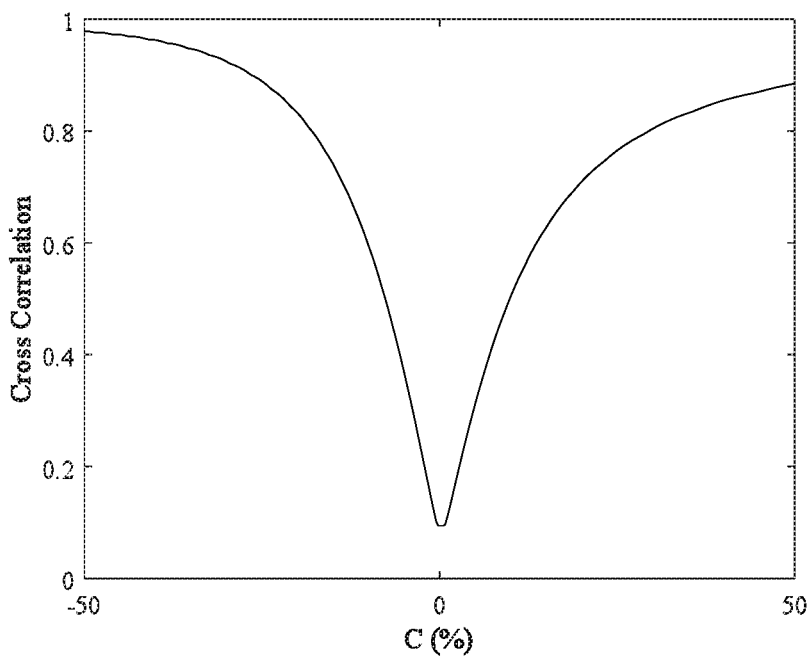
FIG. 27 demonstrates the curve for RCC values, identifying the propagation speed by minimizing the value of RCC.

As discussed above, theoretically a minimum value of Rcc corresponds to the correct propagation speed. Thus, in the disclosed adaptive PSS algorithm an iteration scheme is carried out by trying different propagation speeds until a local minimum in Rcc is obtained. FIG. 27 demonstrates the curve for $R_{CC}$ values, identifying the propagation speed by minimizing the value of $R_{CC}$. A local minimum at 409 m/s was found, which matches the correct speed, indicating a minimal correlation between two separated source signals.

Effect of Source Locations

Unlike propagation speed, errors in distances between sources and sensors affect both amplitudes and phase estimations. For example, if $R_{12}$, which is the distance between the $1^{st}$ sensor and the $2^{nd}$ source, is larger than the "true" value, PSS will force the signal to decay more than it actually decays. Accordingly, contributions from the $2^{nd}$ source to $1^{st}$ sensor will be diminished and arrival time be prolonged, leading to an erroneous mixing of the $1^{st}$ source signal with the $2^{nd}$ one.

To examine the impact of source location errors on separation results, four relative distances $R_{11}$, $R_{12}$, $R_{21}$, and $R_{22}$ are considered. Without loss of generality, each distance is arbitrarily varying over ±50% with respect to its "true" value systematically, and resultant cross correlations of two separated signals are calculated.

Figure 28:
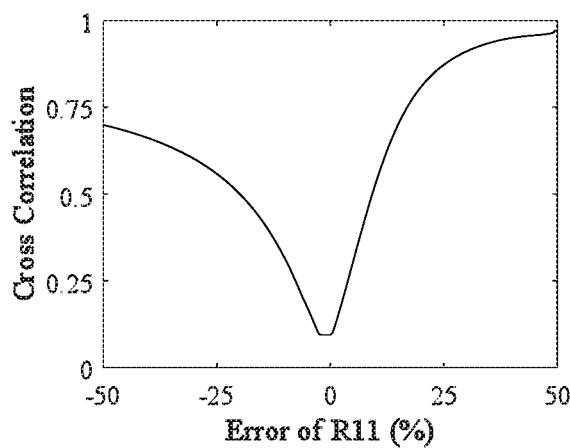
FIG. 28 displays the iteration results of RCC values corresponding to variations of these distances around their true values.
Figure 28:
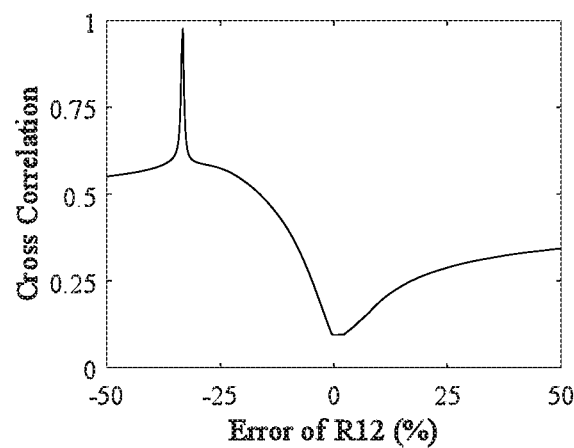
Figure 28:
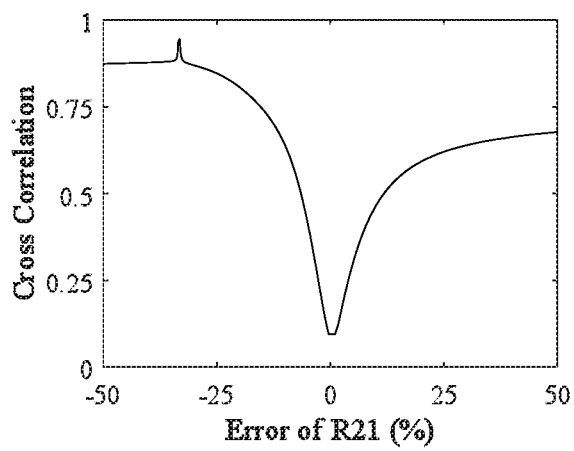
Figure 28:
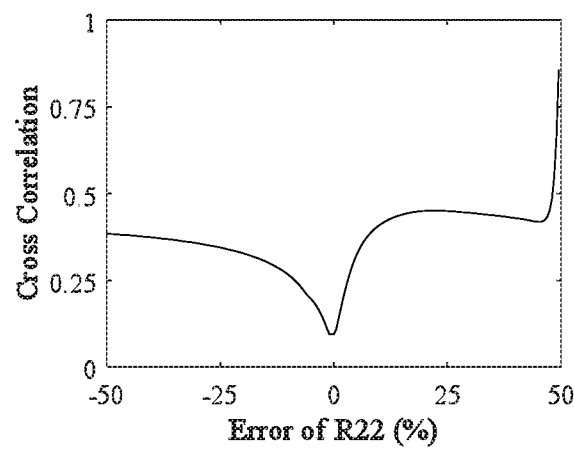

FIG. 28 displays the iteration results of $R_{CC}$ values corresponding to variations of these distances around their true values. Again, there is a local minimum that corresponds to the correct distance in each case, which matches the error analyses as described above. Note that when $R_{11}/R_{12}$=$R_{21}/R_{22}$, there is a maximum peak that indicates a high correlation between the separated signals. These peaks should naturally be ignored as the search is for a local minimum in $R_{CC}$.

Thus, error analyses and corresponding numerical simulation results show that:

1) When the distance between a sensor and source is specified correctly, the accuracy in source separation can be affected by the choice of signal propagation speed. The correct signal propagation speed always corresponds to a local minimum in $R_{CC}$.

2) For a given signal propagation speed, the accuracy in source separation is affected by the relative positions of sources and sensors. Changing sources around sensors in the space will generate several local minimum values $R_{CC}$, one of which will be the correct source position. Selection of this correct source position is now considered.

Use Adaptive PSS Algorithms to Separate Heart Sounds

Heart sounds are caused by the opening and closing of mitral, tricuspid, aortic and pulmonary valves. In healthy adults, and as discussed in detail above, there are two normal heart sounds described as the $1^{st}$ heart sound ($S_1$) and $2^{nd}$ heart sound ($S_2$). The genesis of $S_1$ is related to mitral and tricuspid valve closure sounds, traditionally designated as M1 and T1. The genesis of $S_2$ is related to aortic and pulmonary valve closure sounds, traditionally designated as A2 and P2.

Since the mitral and tricuspid valves as well as the aortic and pulmonary valves are very close to each other, the time differences among them are typically very small. Results have shown that M1 and T1 signals as well as A2 and P2 signals overlap not only in time, but also in frequency domains. Therefore, separating these signals can be challenging. Moreover, the relative distances among these valves differ in general for different patients, plus the fluid medium is confined and non-homogeneous.

According to the disclosure, it is possible to get an approximate solution to separate these signals by using an adaptive PSS algorithm based on an iterative scheme. Once this is done, it is possible to create an effective mathematical model to correlate the sounds due to closings of mitral, tricuspid, aortic and pulmonary valves to blood pressure.

Figure 29:
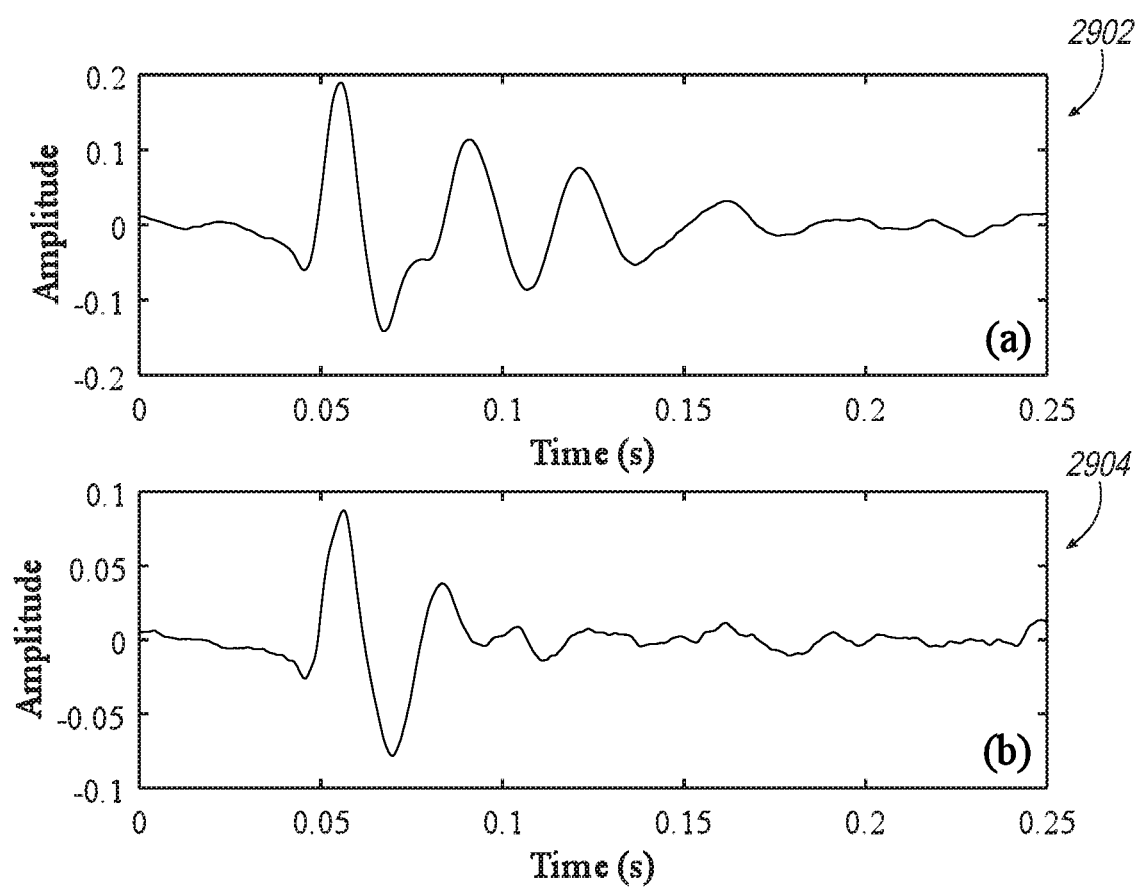
FIG. 29 shows the de-noised S2 signals collected by two sensors.

Thus, optimal sensor locations are selected, and experience shows that the components of $S_2$ are heard with the diaphragm of a stethoscope placed over the left second interspace close to the sternal border. A2 sound is transmitted to the right second interspace, along the left and right sternal border, and to the cardiac apex. P2 is heard over the upper left sternal border. Hence, sensors are placed at the $2^{nd}$ and $3^{rd}$ interspace close to left and right sternal border, respectively. FIG. 29 shows the de-noised $S_2$ signals collected by two sensors, with FIG. 29(a) 2902: As measured by sensor #1; and FIG. 29(b) 2904: As measured by sensor #2

Results demonstrate that by using the disclosed iterative scheme, the propagation speed was found to be c=214 cm/s, and the relative distances between the 1$^{st}$ sensor and A2 and P2 were $R_{11}$=3.105 cm and $R_{12}$=3.5 cm, respectively; and those between the 2$^{nd}$ sensor and A2 and P2 were $R_{21}$=1.85 cm and $R_{22}$=3 cm, respectively.

Figure 30:
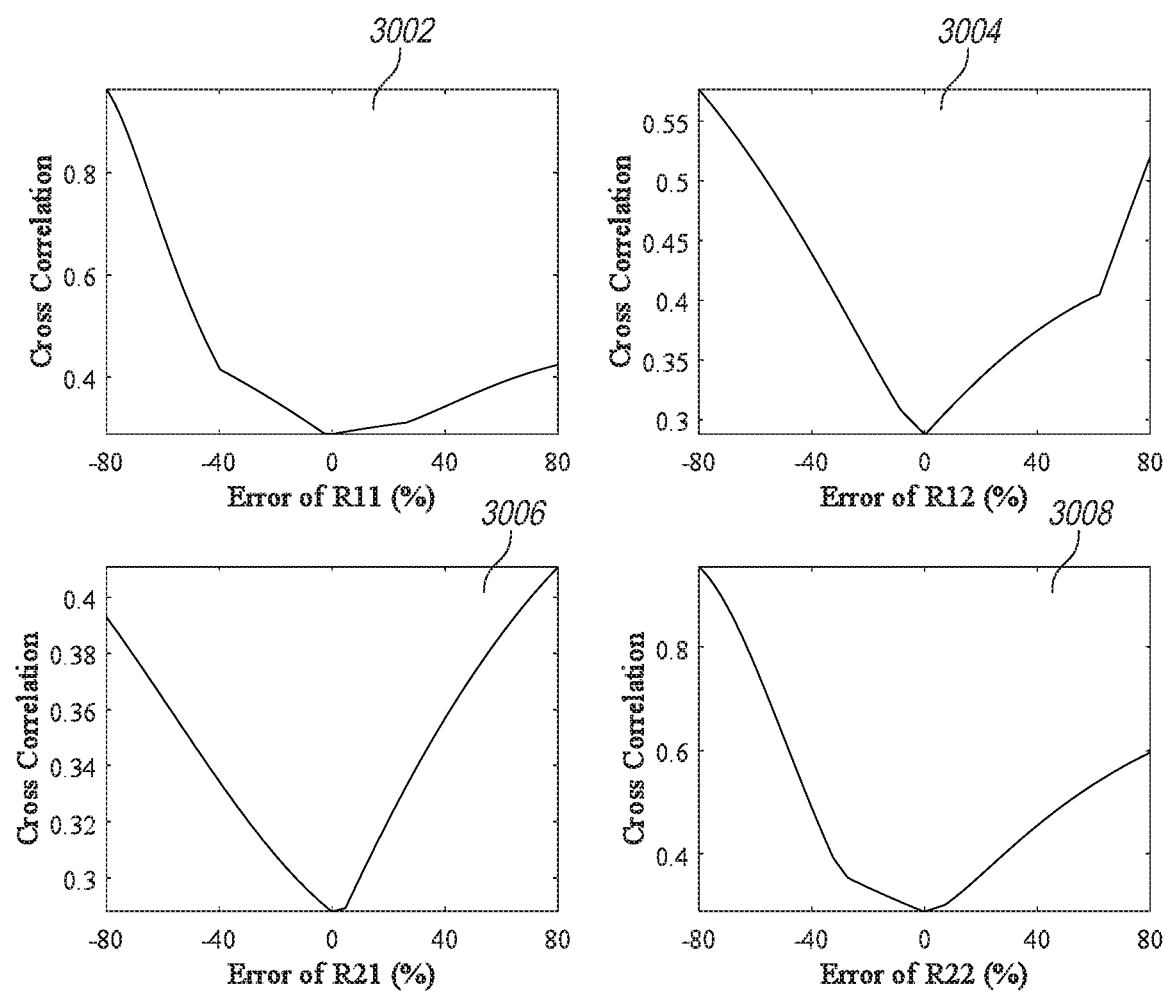
FIG. 30 displays that at the identified distances the cross correlations of separated sounds were minimum.

These results correspond to the minimum cross correlation of the separated heart sounds results, namely, the separated signals were indeed different. FIG. 30 displays that at the identified distances $R_{11}$=3.105 cm 3002, $R_{12}$=3.5 cm 3004, $R_{21}$=1.85 cm 3006, and $R_{22}$=3 cm 3008, the cross correlations of separated sounds were minimum, matching the error analysis result given above, showing the impact of source location on heart sound separation results.

Figure 31:
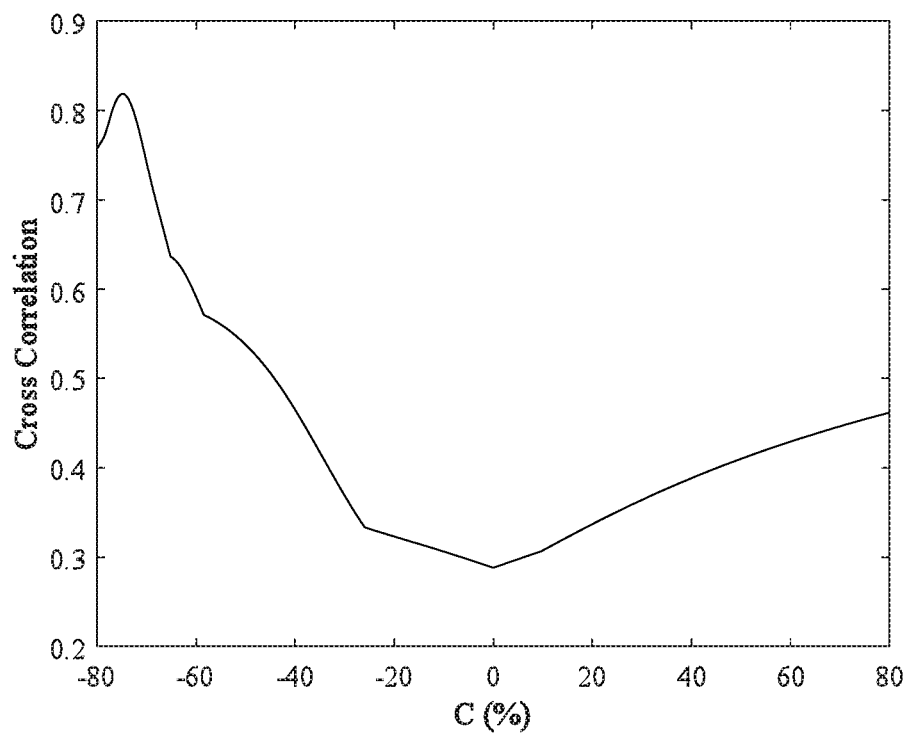
FIG. 31 shows the impact of signal velocity on heart sound separation results.
Figure 32:
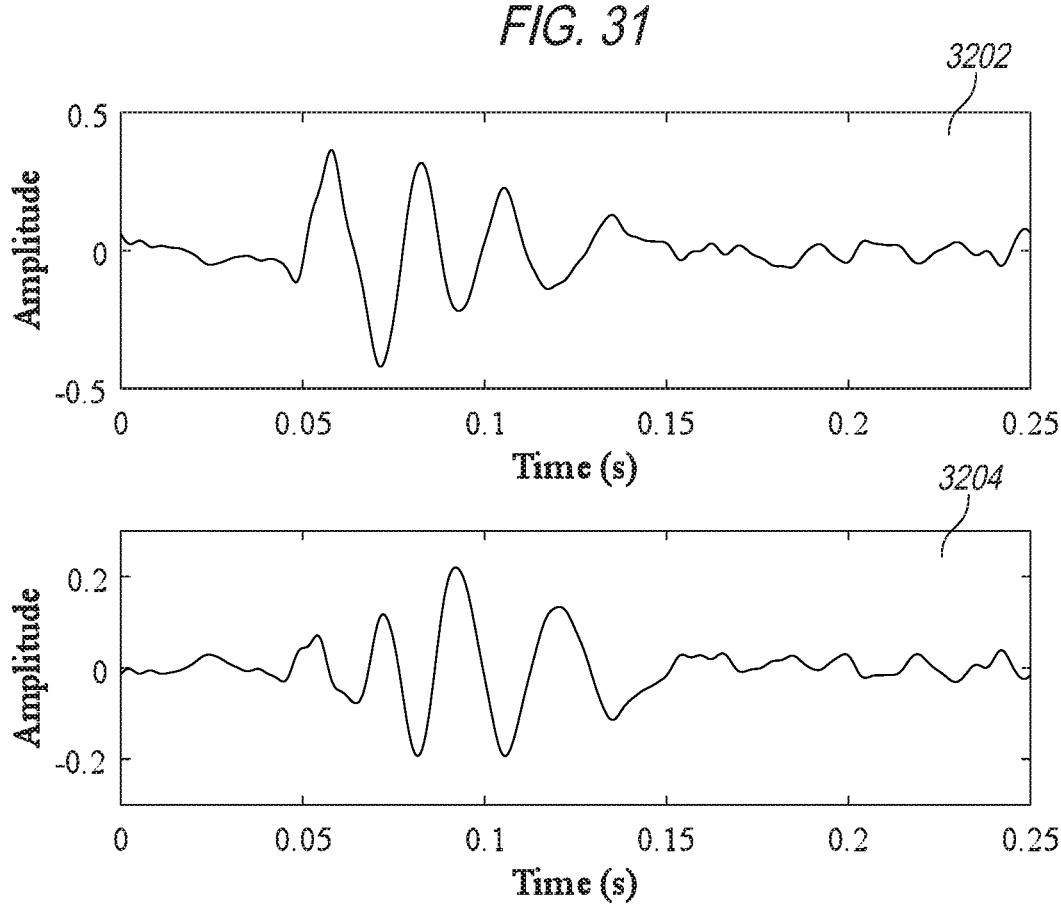
FIG. 32 demonstrates the separated A2 and P2 signals from S2 sounds.

Similarly, FIG. 31 shows that at the identified propagation speed c=214 cm/s, the cross correlations of separated sounds were minimum as well, showing the impact of signal velocity on heart sound separation results. FIG. 32 demonstrates the separated A2 and P2 signals from $S_2$ sounds, showing separated A2 (Top) 3202 and P2 (Bottom) 3204 signals from $S_2$ sound.

Conclusion

In essence, source separation by PSS algorithm is accomplished via deconvolution. Basically, there are two different kinds of deconvolution. The first kind seeks to know at least one of convoluted signals. Such a problem is relatively easy to solve and always has an exact solution. The second kind is a blind separation, without knowing convolved signals and is more difficult to solve. More often than not, certain conditions or additional information of target data will be needed, as in any inverse problems. Otherwise, solutions can be unbounded.

The original PSS algorithm belongs to the first kind of deconvolution, which seeks to know the signal propagation speed and special relationship between sources and sensors. The adaptive PSS algorithm belongs to a completely blind source separation process. To ensure a success, some assumptions or initial guesses are made. There are different types of known BSS. Most of the known BSS approaches rely on probabilities and their results are randomly presented after each run. There is no known knowledge of correlations among separated signals and their respective sources.

Unlike the previous BSS algorithms, the disclosed adaptive PSS algorithms enable one to obtain unique separation results and definitive correlations among separated signals and their respective sources. All that is done is to make some informed educated guesses of some unknown variables and their accuracies can almost be ensured by an iteration process. As an example, adaptive PSS algorithms are applied to separate components of heart sounds measured directly from patients. The separated signals have led to a successful prediction of the patients' blood pressures that are correlated well with cuff measurement results, generally considered to be the 'gold standard' for random BP measurement.

However, adaptive PSS algorithms involve a multivariate optimization process to minimize all off-diagonal terms in the cross-correlation matrix simultaneously by applying deconvolution repeatedly. Consequently, this approach can be time consuming, especially when three or more sources need to be separated. This is the major downside of the present adaptive PSS algorithms that must be circumvented in order for this approach to expand potential applications in practice.

Figure 33:
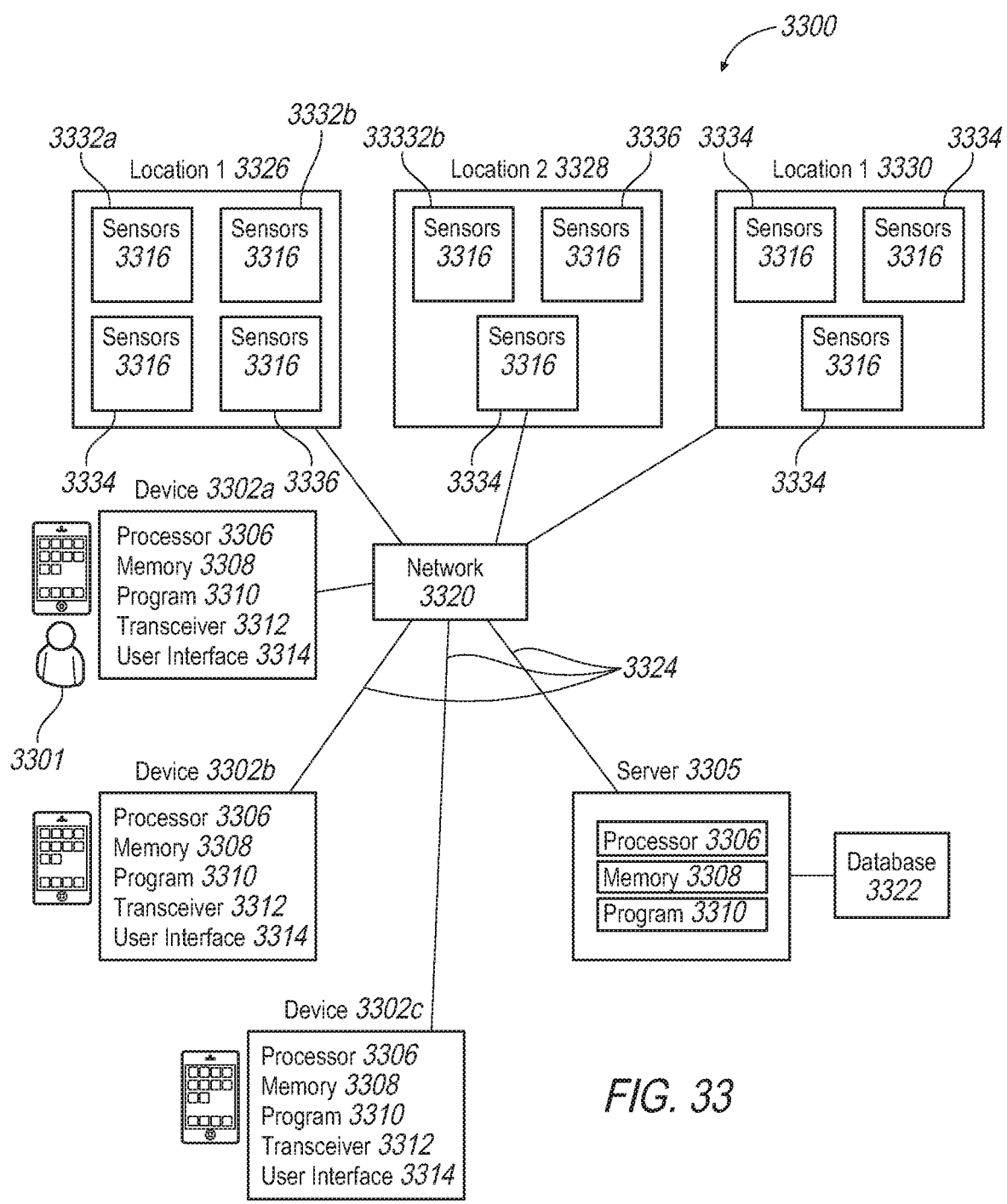
FIG. 33 illustrates an exemplary system for implementing the disclosed subject matter.

FIG. 33 illustrates an exemplary system 3300, for example, to obtaining and communicating BP information based on various locations, under different conditions, using for instance a WIFI system. That is, system 3300 may be implemented by taking heart sound measurements at one location, and analyzed at the location where the heart sounds are taken, or at an entirely different location. System 3300 may take many different forms and include multiple and/or hardware components and facilities. While an exemplary system 3300 is shown in FIG. 33, the exemplary components illustrated are not intended to be limiting, may be optional, and are not essential to any other component or portion of system 3300. Indeed, additional or alternative components and/or implementations may be used.

System 3300 may include or be configured to be utilized by a user 3301 such as a healthcare worker, an engineer, statistician, or data processing technician. System 3300 may include one or more of computing devices 3302a, 3302b, 3302c, server 3305, processor 3306, memory 3308, program 3310, transceiver 3312, user interface 3314, sensors 3316, network 3320, database 3322, and connections 3324. Device 3302 may include any or all of device 3302a (e.g., a desktop, laptop, or tablet computer), device 3302b (e.g., a mobile or cellular phone), and device 3302c (e.g., a mobile or cellular phone). Processor 3306 may include a hardware processor that executes program 3310 to provide any or all of the operations described herein (e.g., by device 3302, server 3305, database 3322, or any combination thereof) and that are stored as instructions on memory 3308 (e.g., of device 3302, server 3305, or any combination thereof).

An exemplary system 3300 may include user interface 3314, processor 3306, and memory 3308 having program 3310 communicatively connected to processor 3306. System 3300 may further include transceiver 3312 that may be communicatively connected to one or a plurality of sensors 3316 associated with each of a plurality of patients. For instance, system 3300 may include a first location 3326, a second location 3328, and a third location 3330 may, each of which may include one or more sound measurement devices that may be applied to a chest of a patient to obtain heart sounds.

Second location 3328, representative of a different healthcare facility than that of first location 3326, may be either a different building within the same plot of land, a different state or country. Third location 3330, similarly, may be representative of yet a different healthcare facility, and may be a different building within the same plot of land. In fact, any of locations 3326, 3328, 3330 may be at home for an in-home patient monitoring arrangement, or within a vehicle having a patient therein with sensors 3316 positioned to measure heart sounds and obtain BP measurements, according to the disclosure, in real-time.

System 3300 using processor 3306 may provide operations that include displaying by way of user interface 3314 statistics and other data related to usage of each of devices 3332, 3334, and 3336. That is, each of devices 3332, 3334, 3336 may have input thereto, as will be further described, via sensors 3316. Sensors 3316 may generally be exemplary sensor 1200 (having an accelerometer with decoupled piezoelectric layer) of FIG. 12, used for the disclosed method. System 3300 may also communication between locations, such that algorithms for BP measurement may be obtained or developed at one location, and implemented at another. That is, user 3301 may update BP parameters having operational instructions and various coefficients for BP determination, in device 3302a, device 3302b, and/or device 3302c.

System 3300 may include an overall network infrastructure through which any of devices 3302, server 3305, and database 3322 may communicate, for example, to transfer information between any portion of system 3300 using connections 3324. In general, a network (e.g., system 3300 or network 3320) may be a collection of computing devices and other hardware to provide connections and carry communications. Devices 3302 may include any computing device such as a mobile device, cellular phone, smartphone, smartwatch, activity tracker, tablet computer, next generation portable device, handheld computer, notebook, laptop, projector device, or virtual reality or augmented reality device. Devices 3302 may include processor 3306 that executes program 3310. Devices 3302 may include memory 3308 that stores model, setting, and other information, and program 3310. Devices 3302 may include transceiver 3312 that communicates information between any of devices 3302, sensors 3316, server 3305, and database 3322.

Server 3305 may include any computing system. Server 3305 may generate by processor 3306, program 3310 and store information by memory 3308, e.g., information particular to each of devices 3332, 3334, 3336. Server 3305 may communicatively connect with and transfer information with respect to devices 3302, sensors 3316, and database 3322. Server 3305 may be in continuous or periodic communication with devices 3302, sensors 3316, and database 3322. Server 3305 may include a local, remote, or cloud-based server or a combination thereof and may be in communication with and provide information (e.g., as part of memory 3308 or database 3322) to any or a combination of devices 3302. Server 3305 may further provide a web-based user interface (e.g., an internet portal) to be displayed by user interface 3314. Server 3305 may communicate the information with devices 3302 using a notification including, for example automated phone call, short message service (SMS) or text message, e-mail, http link, web-based portal, or any other type of electronic communication. In addition, server 3305 may be configured to store information as part of memory 3308 or database 3322. Server 3305 may include a single or a plurality of centrally or geographically distributed servers 3305. Server 3305 may be configured to store and coordinate information with and between any of devices 3302, and database 3322. System 3300, or any portion of system 3300 such as devices 3332, 3334, 3336, may include one or more sensors 3316 configured to receive sensor inputs and provide sensor outputs, e.g., including usage information associated with BP monitoring devices.

User interface 3314 of devices 3302 may include any user interface device, display device, or other hardware mechanism that connects to a display or supports user interfaces so as to communicate and present information throughout the system 3300. User interface 3314 may include any input or output device to facilitate receipt or presentation of information in audio or visual form, or a combination thereof. Examples of a display may include, without limitation, a touchscreen, cathode ray tube display, light-emitting diode display, electroluminescent display, electronic paper, plasma display panel, liquid crystal display, high-performance addressing display, thin-film transistor display, organic light-emitting diode display, surface-conduction electron-emitter display, laser TV, carbon nanotubes, quantum dot display, interferometric modulator display, projector device, and the like. User interface 3314 may present information to any user of devices 3302.

Connections 3324 may be any wired or wireless connections between two or more endpoints (e.g., devices or systems), for example, to facilitate transfer of BP information, to facilitate upgradeable enhancements to devices, such as wirelessly or via wired connections. Connection 3324 may include a local area network, for example, to communicatively connect the devices 3302 with network 3320. Connection 3324 may include a wide area network connection, for example, to communicatively connect server 3305 with network 3320. Connection 3324 may include a wireless connection, e.g., radiofrequency (RF), near field communication (NFC), Bluetooth communication, WIFI, or a wired connection, for example, to communicatively connect the devices 3302, and sensors 3316.

Any portion of system 3300, e.g., devices 3302 and server 3305, may include a computing system and/or device that includes a processor 3306 and a memory 3308. Computing systems and/or devices generally include computer-executable instructions, where the instructions may define operations and may be executable by one or more devices such as those listed herein. Computer-executable instructions may be compiled or interpreted from computer programs created using a variety of programming languages and/or technologies, including, without limitation, and either alone or in combination, Java language, C, C++, Visual Basic, Java Script, Perl, SQL, PL/SQL, Shell Scripts, Unity language, etc. System 300, e.g., devices 302 and server 305 may take many different forms and include multiple and/or alternate components and facilities, as illustrated in the Figures. While exemplary systems, devices, modules, and sub-modules are shown in the Figures, the exemplary components illustrated in the Figures are not intended to be limiting. Indeed, additional or alternative components and/or implementations may be used, and thus the above communication operation examples should not be construed as limiting.

In general, computing systems and/or devices (e.g., devices 3302 and server 3305) may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., the BlackBerry OS distributed by Research In Motion of Waterloo, Canada, and the Android operating system developed by the Open Handset Alliance. Examples of computing systems and/or devices such as devices 302, and server 305 may include, without limitation, mobile devices, cellular phones, smart-phones, super-phones, next generation portable devices, mobile printers, handheld or desktop computers, notebooks, laptops, tablets, wearables, virtual or augmented reality devices, secure voice communication equipment, networking hardware, computer workstations, or any other computing system and/or device.

Further, processors such as processor 3306 receive instructions from memories such as memory 3308 or database 3322 and execute the instructions to provide the operations herein, thereby performing one or more processes, including one or more of the processes described herein. Such instructions and other guidance information may be stored and transmitted using a variety of computer-readable mediums (e.g., memory 3308 or database 3322). Processors such as processor 3306 may include any computer hardware or combination of computer hardware that is configured to accomplish the purpose of the devices, systems, operations, and processes described herein. For example, processor 3306 may be any one of, but not limited to single, dual, triple, or quad core processors (on one single chip), graphics processing units, and visual processing hardware.

A memory such as memory 3308 or database 3322 may include, in general, any computer-readable medium (also referred to as a processor-readable medium) that may include any non-transitory (e.g., tangible) medium that participates in providing guidance information or instructions that may be read by a computer (e.g., by the processors 3306 of the devices 3302 and server 3305). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including radio waves, metal wire, fiber optics, and the like, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Further, databases, data repositories or other guidance information stores (e.g., memory 3308 and database 3322) described herein may generally include various kinds of mechanisms for storing, providing, accessing, and retrieving various kinds of guidance information, including a hierarchical database, a set of files in a file system, an application database in a proprietary format, a relational database management system (RDBMS), etc. Each such guidance information store may generally be included within (e.g., memory 3308) or external (e.g., database 3322) to a computing system and/or device (e.g., devices 3302 and server 3305) employing a computer operating system such as one of those mentioned above, and/or accessed via a network (e.g., system 3300 or network 3320) or connection in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above. Memory 3308 and database 3322 may be connected to or part of any portion of system 3300.

Thus, disclosed herein is a method and system for that includes:

Developing a sensitive, reliable and easy to use technology for continuous and random/intermittent non-invasive BP monitoring. An accelerometer is disclosed with a decoupled piezo-resistive layer that can be taped easily on the patient's chest to provide a non-invasive method for heart sound measurements with a high sensitivity. A computer model is developed that can take the output from the accelerometer to analyze heart sounds, correlate them to BP, and calculate BP on a continuous basis in real time. Advantages of the disclosed subject matter includes but is not limited to: 1) heart sounds are much easier and more reliable to measure, regardless of the patient's age, size, sex, etc. than direct BP measurements; 2) the measurement device is easy to apply and BP calculations have statistically-significant accuracy, precision, specificity and sensitivity; and, 3) it will mitigate the inaccuracy in existing conventional BP measurements.

The disclosed subject matter represents an advancement over the currently identified and known limitations of various methods of BP measurement including the potential to provide a better estimate of central aortic pressure, which is disclosed as a more accurate measurement of individual BP.

The disclosed system and method:

a. enables the prediction of blood pressures (BP) based on the heart sounds measured directly on the chest of a patient using piezoelectric sensors, using detailed evaluation of the components of the of the heart sounds and their correlation with BP.

b. includes an algorithm that is then used to estimate BP from the individual heart sounds. The BP readings as measured provide an estimate of BP, which is an indicator of individual risk for morbidity and mortality associated with high BP.

c. is objective and standardized and not dependent on current variables such as cuff size, cuff pressures, arm thickness, having the arm at heart height, and if a stethoscope is used is not dependent on the testers hearing (which can vary from person to person and/or be different for the same person over time).

d. provides an easy and economical way of measuring 24 hour ambulatory BP.

e. has global implications and is a good way for low income and or rural patients to have accurate BP determinations.

f. is easy to comply with HIPAA and PHI implication as determinations can be coded to ensure patient privacy.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope of the disclosure should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the disclosure is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A method of determining blood pressure, comprising:
    measuring heart sounds through transducers on an outer surface of a chest;
    separating the measured heart sounds into a first heart sound ($S_1$) and a second heart sound ($S_2$);
    mathematically characterizing $S_1$ and $S_2$;
    determining a blood pressure based on the characterization;
    denoising the heart sounds;
    determining a heart rate; and
    segmenting the heart sounds to identify $S_1$ and $S_2$;
    wherein denoising $S_1$ and $S_2$ comprises determining a propagation speed of signal propagation within a patient by iteratively varying an assumed distance between a sensor and a heart valve; and
    identifying $S_1$ and $S_2$ based on the determination of the propagation speed of signal propagation.

2. The method of claim 1, wherein determining the propagation speed includes establishing an influence matrix that identifies an optimal influence matrix to separate source signals.

3. The method of claim 1, wherein separating the measured heart sounds into $S_1$ and $S_2$ further comprises:
    applying an autocorrelation function to the denoised heart sounds to generate correlated $S_1$ and $S_2$ sounds;
    applying a moving window based on a normal heart beat to the correlated $S_1$ and $S_2$ sounds;
    retaining $S_1$ peaks and discarding two peaks between the $S_1$ peaks; and
    calculating an average interval between at least two of the $S_1$ peaks.

4. The method of claim 1,
    wherein segmenting the heart sounds to identify $S_1$ and $S_2$ comprises:
    selecting a resampling window based on the determined heart rate;
    resampling the measured heart sounds to identify local maxima and a maximum peak in a cardiac cycle;
    determining a duration between the local maxima; and
    determining which of the local maxima represents $S_1$ and which represents $S_2$ based on a duration between the local maxima, based on an interval $S_1$ to $S_2$ that is known to be smaller than an interval of $S_2$ to $S_1$.

5. The method of claim 1, wherein mathematically characterizing $S_1$ and $S_2$ further comprises calculating growth rates and decay rates from $S_1$ and $S_2$.

6. The method of claim 1, wherein determining a blood pressure based on the characterization of $S_1$ and $S_2$ is continuous.

7. A non-transitory computer-readable medium tangibly embodying computer-executable instructions of a program being executable by a hardware processor of a computing device with a user interface to provide operations comprising:
    measuring heart sounds through non-invasive transducers;
    separating the measured heart sounds into a first heart sound ($S_1$) and a second heart sound ($S_2$);
    mathematically characterizing $S_1$ and $S_2$;
    determining a blood pressure based on the characterization;
    denoising the heart sounds;
    determining a heart rate; and
    segmenting the heart sounds to identify $S_1$ and $S_2$;
    wherein the denoising instructions for denoising $S_1$ and $S_2$ further comprise:
    determining a propagation speed of signal propagation within a patient by iteratively varying an assumed distance between a sensor and a heart valve; and
    identifying $S_1$ and $S_2$ based on the determination of the propagation speed of signal propagation.

8. The computer-readable medium of claim 7, wherein the instructions for determining the propagation speed further comprise instructions to establish an influence matrix that identifies an optimal influence matrix to separate source signals.

9. The computer-readable medium of claim 7, wherein the instructions separating the measured heart sounds into $S_1$ and $S_2$ further comprise instructions to:
    apply an autocorrelation function to the denoised heart sounds to generate correlated $S_1$ and $S_2$ sounds;
    apply a moving window based on a normal heart beat to the correlated $S_1$ and $S_2$ sounds;
    retain $S_1$ peaks and discarding two peaks between the $S_1$ peaks; and
    calculate an average interval between at least two of the $S_1$ peaks.

10. The computer-readable medium of claim 7,
    wherein the instructions segmenting the heart sounds to identify $S_1$ and $S_2$ further comprise instructions to:
    select a resampling window based on the determined heart rate;
    resample the measured heart sounds to identify local maxima and a maximum peak in a cardiac cycle;
    determine a duration between the local maxima; and
    determine which of the local maxima represents $S_1$ and which represents $S_2$ based on a duration between the local maxima, based on an interval $S_1$ to $S_2$ that is known to be smaller than an interval of $S_2$ to $S_1$.

11. The computer-readable medium of claim 7, wherein the instructions mathematically characterizing $S_1$ and $S_2$ further comprise instructions to calculate growth rates and a decay rates from $S_1$ and $S_2$.

12. The computer-readable medium of claim 7, wherein determining a blood pressure based on the characterization of $S_1$ and $S_2$ is continuous.

13. A system for measuring blood pressure, comprising:
    a sensor configured non-invasively and positioned on a chest area to acquire heart sounds; and
    a computer coupled to the sensor, the computer configured to:
    measure heart sounds;
    separate the measured heart sounds into a first heart sound ($S_1$) and a second heart sound ($S_2$);
    mathematically characterize $S_1$ and $S_2$;
    determine a blood pressure based on the characterization;
    denoise the heart sounds;
    determine a heart rate; and
    segment the heart sounds to identify $S_1$ and $S_2$;
    wherein the denoising further comprises the computer configured to:
    determine a propagation speed of signal propagation within a patient by iteratively varying an assumed distance between a sensor and a heart valve; and
    identify $S_1$ and $S_2$ based on the determination of the propagation speed of signal propagation; and
    wherein the instructions to determine the propagation speed include the computer configured to establish an influence matrix that identifies an optimal influence matrix to separate source signals.

14. The system of claim 13, wherein separating the measured heart sounds into $S_1$ and $S_2$ further comprises the computer configured to:

apply an autocorrelation function to the denoised heart sounds to generate correlated $S_1$ and $S_2$ sounds;

apply a moving window based on a normal heart beat to the correlated $S_1$ and $S_2$ sounds;

retain $S_1$ peaks and discarding two peaks between the $S_1$ peaks; and calculate an average interval between at least two of the $S_1$ peaks.

15. The system of claim 13, wherein segmenting the heart sounds to identify $S_1$ and $S_2$ further comprises the computer configured to:

select a resampling window based on the determined heart rate;

resample the measured heart sounds to identify local maxima and a maximum peak in a cardiac cycle;

determine a duration between the local maxima; and determine which of the local maxima represents $S_1$ and which represents $S_2$ based on a duration between the local maxima, based on an interval $S_1$ to $S_2$ that is known to be smaller than an interval of $S_2$ to $S_1$.

16. The system of claim 13, wherein mathematically characterizing $S_1$ and $S_2$ further comprises the computer configured to calculate growth rates and a decay rates from $S_1$ and $S_2$.

17. The system of claim 13, wherein determining a blood pressure based on the characterization of $S_1$ and $S_2$ is continuous.

18. A method of determining blood pressure, comprising:
measuring heart sounds through transducers on an outer surface of a chest;
separating the measured heart sounds into a first heart sound ($S_1$) and a second heart sound ($S_2$);
mathematically characterizing $S_1$ and $S_2$;
determining a blood pressure based on the characterization;
denoising the heart sounds;
determining a heart rate; and
segmenting the heart sounds to identify $S_1$ and $S_2$;
wherein segmenting the heart sounds to identify $S_1$ and $S_2$ comprises:
selecting a resampling window based on the determined heart rate;
resampling the measured heart sounds to identify local maxima and a maximum peak in a cardiac cycle;
determining a duration between the local maxima; and
determining which of the local maxima represents $S_1$ and which represents $S_2$ based on a duration between the local maxima, based on an interval $S_1$ to $S_2$ that is known to be smaller than an interval of $S_2$ to $S_1$.

19. A non-transitory computer-readable medium tangibly embodying computer-executable instructions of a program being executable by a hardware processor of a computing device with a user interface to provide operations comprising:

measuring heart sounds through non-invasive transducers;
separating the measured heart sounds into a first heart sound ($S_1$) and a second heart sound ($S_2$);
mathematically characterizing $S_1$ and $S_2$;
determining a blood pressure based on the characterization;
denoising the heart sounds;
determining a heart rate; and
segmenting the heart sounds to identify $S_1$ and $S_2$; and
wherein the instructions segmenting the heart sounds to identify $S_1$ and $S_2$ further comprise instructions to:
select a resampling window based on the determined heart rate;
resample the measured heart sounds to identify local maxima and a maximum peak in a cardiac cycle;
determine a duration between the local maxima; and
determine which of the local maxima represents $S_1$ and which represents $S_2$ based on a duration between the local maxima, based on an interval $S_1$ to $S_2$ that is known to be smaller than an interval of $S_2$ to $S_1$.

20. A system for measuring blood pressure, comprising:
a sensor configured non-invasively and positioned on a chest area to acquire heart sounds; and
a computer coupled to the sensor, the computer configured to:
measure heart sounds;
separate the measured heart sounds into a first heart sound ($S_1$) and a second heart sound ($S_2$);
mathematically characterize $S_1$ and $S_2$;
determine a blood pressure based on the characterization;
denoise the heart sounds;
determine a heart rate; and
segment the heart sounds to identify $S_1$ and $S_2$;
wherein segmenting the heart sounds to identify $S_1$ and $S_2$ further comprises the computer configured to:
select a resampling window based on the determined heart rate;
resample the measured heart sounds to identify local maxima and a maximum peak in a cardiac cycle;
determine a duration between the local maxima; and
determine which of the local maxima represents $S_1$ and which represents $S_2$ based on a duration between the local maxima, based on an interval $S_1$ to $S_2$ that is known to be smaller than an interval of $S_2$ to $S_1$.

* * * * *